US005936080A

United States Patent [19]
Stec et al.

[11] Patent Number: 5,936,080
[45] Date of Patent: Aug. 10, 1999

[54] COMPOSITIONS AND METHODS FOR THE SYNTHESIS OF ORGANOPHOSPHORUS DERIVATIVES

[75] Inventors: Wojciech J. Stec, Ksawerów; Lucyna Woźniak, Lódź, both of Poland

[73] Assignees: Genta Incorporated, San Diego, Calif.; Polska Akademia Nauk, Lodz, Poland

[21] Appl. No.: 08/653,204

[22] Filed: May 24, 1996

[51] Int. Cl.$^6$ .................................................. C07H 19/04
[52] U.S. Cl. ........................ 536/26.7; 536/26.1; 536/26.8
[58] Field of Search ................................ 536/26.8, 26.7, 536/26.1

[56] References Cited

PUBLICATIONS

Bryant et al., (1979) *Stereochemical Course of the Reaction Catalyzed by 5'–Nucleotide Phosphodiesterase from Snake Venom*, Biochemistry 18(13), 2825–2828.
Cormier, et al., (1988) *Synthesis of hexanucleotide analogues containing diisopropylsilyl internucleotide linkages*, Nucleic Acids Research 16(10), 4583–4595.
John Goodchild, (1990) *Conjugates of Oligonucleotides and Modified Oligonucleotides: A Review of Their Synthesis and Properties*, Bioconjugate Chem., 1(3), 166–187.
Lesnikowski, et al., (1988) *Stereoselective synthesis of P–homochiral oligo(thymidine methanephosphonates)*, Nucleic Acids Research 16(24), 11675–11688.
Lesnikowski, et al., (1990) *Octa(thymidine methanephosphonates) of partially defined sterochemistry; synthesis and effect of chirality at phosphorus on binding to pentadecadeoxyriboadenylic acid*, Nucleic Acids Research 18(8), 2109–2115.
Lesnikowski, et al., (1991) *Stereospecific Synthesis of P–Chiral Di(2'–O–Deoxyribonucleoside) Mehtanephosphonates*, Nucleosides & Nucleotides, 10(1–3), 733–736.
Loke, et al., (1988), *Delivery of c–myc Antisense Phosphorothioate Oligodeoxynucleotides to Hematopoietic Cells in Culture by Liposome Fusion: Specific reduction in c–myc Protein Expression Correlates with Inhibition of Cell Growth and DNA Synthesis*, Curr. Topics in Microbiol. and immunol. 141, 282–289.
Loschner, et al. (1989), *One Pot $R_P$–Diastereoselective Synthesis of Dinucleoside Methylphosphonates Using Methyldichlorophosphine*, Tetrahedron Lett. 30(41), 5587–5590.
Engels, et al., (1991), *Diastereoselective Synthesis of Thymidine–Methylphosphonate Dimers*, Nucleosides & Nucleotides, 10(1–3), 347–350.
Marcus–Sekura, et al., (1987), *Comparative inhibition of chloramphenicol acetyltransferase gene expression by antisense oligonucleotide analogues having alkyl phosphotriester, methylphosphonate and phosphorothioate linkages*, Nucleic Acids Research, 15(14), 5749–5763.
Mark Matteucci, (1990), *Deoxyoligonucleotide Analogs Based on Formacetal Linkages*, Tetrahedron Lett. 31(17), 2385–2388.
Mazur, et al., (1984), *Isosteres of Natural Phosphates. 11. Synthesis of A Phosphonic Acid Analogue of An Oligonucleotide*, Tetrahedron Lett. 40(20), 3949–3956.

Miller, et al., (1977), *Effects of a Trinucleotide Ethyl Phosphotriester, G'''p(Et)G'''p(Et)U, on Mammalian Cells in Culture*, Biochemistry, 16(9), 1988–1996.
Potter, et al., (1983), *Synthesis and Configurational Analysis of a Dinucleoside Phosphate Isotopically Chiral at Phosphorus. Stereochemical Course of Penicillium citrum Nuclease P1 Reaction*, Biochemistry 22, 1369–1377.
Stirchak, et al., (1987), *Uncharged Stereoregular Nucleic Acid Analogues. 1. Synthesis of a Cytosine–Containing Oligomer with Carbamate Internucleoside Linkages*, J. Org. Chem., 52, 4202–4206.
David B. Wilson, (1978), *Cellular Transport Mechanisms*, Ann. Rev. Biochem. 47.
Brill, W.K.D. et al, Tetrahedron Letters, 1988, 29(11), pp. 1227–1230.

*Primary Examiner*—Bernard Dentz
*Attorney, Agent, or Firm*—Knobbe, Martens Olson & Bear LLP

[57] ABSTRACT

New organophosphorus mononucleoside derivatives, methods of their synthesis and methods for the synthesis of organophosphorus dinucleotide derivatives utilizing the organophosphorus mononucleosides are provided. Synthesized organophosphorus mononucleoside derivatives of the present invention are characterized by the formula;

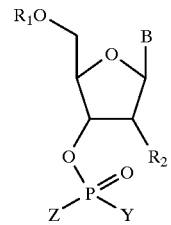

Formula 1

Organophosphorus dinucleoside derivatives prepared from the synthesis methods provided in the present invention are characterized by the formula;

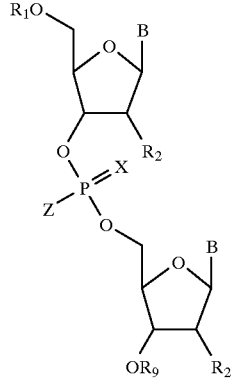

Formula 3

23 Claims, 9 Drawing Sheets

FORMULA 1

FORMULA 2

FORMULA 3

FORMULA 4

FORMULA 5

FORMULA 6A

FORMULA 6B

FORMULA 7A

FORMULA 7B

FORMULA 8A

FORMULA 8B

FORMULA 9A

FORMULA 9B

FORMULA 10A

FORMULA 10B

FORMULA 11A

FORMULA 11B

FORMULA 12

FORMULA 13 ature has focused upon inter
COMPOSITIONS AND METHODS FOR THE SYNTHESIS OF ORGANOPHOSPHORUS DERIVATIVES

CROSS REFERENCE TO RELATED APPLICATIONS

This application is a continuation-in-part of and claims priority from the following Polish patent applications: Polish patent application Ser. No. P-308803 filed May 26, 1995, Polish patent application Ser. No. P-310248 filed Aug. 31, 1995, and Polish patent application Ser. No. P-312934 filed Feb. 26, 1996.

TECHNICAL FIELD

The present invention relates generally to novel organophosphorus mono- and di-nucleoside derivatives and their methods of synthesis.

BACKGROUND OF THE INVENTION

It is well known that most of the bodily states in animals, including disease states, are effected by proteins. Such proteins, either acting directly or through their enzymatic functions contribute to many disease states in animals and man.

Classical therapeutics has generally focused upon interactions with such proteins in an effort to moderate their disease causing or disease potentiating functions. Recently, however, attempts have been made to moderate the actual production of such proteins by interactions with the molecules (i.e. intercellular RNA) that direct their synthesis. These interactions have involved the hybridization of complimentarily "antisense" oligonucleotides or certain analogs thereof to RNA. Hybridization refers to the sequence-specific hydrogen bonding of oligonucleotides or oligonucleotide analogs to RNA or DNA. When hybridization occurs biosynthesis of proteins can be interrupted. This interference with the production of proteins, has been hoped to effect therapeutic results with maximum effect and minimal side effects. Oligonucleotide analogs may also be utilized to moderate the production of proteins by a similar mechanism.

The pharmacological activity of antisense oligonucleotides and oligonucleotide analogs, like other therapeutics, depends on a number of factors that influence the effective concentration of these agents at specific intercellular targets. One important factor for oligonucleotides is the stability of the species in the presence of nucleases. It is unlikely that unmodified oligonucleotides will be useful therapeutic agents because they are rapidly degraded by nucleases. Modifications of oligonucleotides to render them resistant to nucleases therefore are greatly desired.

Modifications of oligonucleotides to enhance nuclease resistance have generally taken place on the phosphorus atom of the sugar-phosphate backbone. Phosphorothioates, methyl phosphonates, phophoramidates, and phosphorotriesters have been reported to confer various levels of nuclease resistance. However, phosphate-modified oligonucleotides of this type generally have suffered from inferior hybridization properties (Cohen, J. S., ed. *Oligonucleotides: Antisense Inhibitors of Gene Expression*, CRC Press, Inc. Boca Raton Fla., 1989).

Another key factor is the ability of antisense compounds to traverse the plasma membrane of specific cells involved in the disease process. Cellular membranes consist of lipid-protein bilayers that are freely permeable to small, nonionic, lipophilic compounds yet inherently impermeable to most natural metabolites and therapeutic agents (Wilson, D. B. *Ann. Rev. Biochem.* 47:933, 1978) The biological and antiviral effects of natural and modified oligonucleotides in cultured mammalian cells have been well documented. Thus, it appears that these agents can penetrate membranes to reach their intercellular targets. Uptake of antisense compounds by a variety of mammalian cells including HL-60, Syrian Hamster fibroblast, U937, L929, CV-1 and ATH8 cells, have been studied using natural oligonucleotides and certain nuclease resistant analogs, such as alkyl triesters (Miller P. S. et al., *Biochem.* 16:1988, 1977); methylphosphonates (Marcus-Sekura, C. H. et al., *Nuc. Acids Res.* 15:5749, 1987; Miller P.S. et al., *Biochem.* 16:1988, 1977; and Loke S. K. et al., *Top. Microbiol. Immunol.* 141:282, 1988).

Modified oligonucleotides and oligonucleotide analogs may be less readily internalized than their natural counterparts. As a result, the activity of many previously available antisense oligonucleotides have not been sufficient for practical therapeutic, research or diagnostic purposes. Two other deficiencies recognized by the prior art are that many of the previously designed oligonucleotide antisense therapeutics hybridize less efficiently to intercellular RNA and lack the defined chemical or enzyme-mediated event to terminate essential RNA function.

Modifications to enhance the effectiveness of the antisense oligonucleotides and overcome these problems have taken many forms. These modifications include base ring modifications, sugar moiety modifications, and sugar-phosphate backbone modifications. Prior sugar-phosphate backbone modifications, particularly on the phosphorus atom, have effected various levels of resistance to nucleases. However, while the ability of an antisense oligonucleotide to bind to specific DNA or RNA with fidelity is fundamental to antisense methodology, modified phosphorus oligonucleotides have generally suffered from inferior hybridization properties.

Replacement of the phosphorus atom has been an alternative approach in attempting to avoid the problems associated with modification on the prochiral phosphate moiety. Some modifications in which replacement of the phosphorus atom has been achieved are discussed by Matteucci, (*Tetrahedron Letters* 31:2385, 1990), wherein replacement of the phosphorus atom with a methylene group is limited by available methodology which does not provide for uniform insertion of the formacetal linkage throughout the backbone, and its instability, making it unsuitable for use; Cormier, (*Nuc. Acids Res.* 16:4583, 1988), wherein replacement of the phosphorus moiety with a diisopropylsilyl moiety is limited by methodology, solubility of the homopolymers and hybridization properties; Stirchak (*J. Org. Chem.* 52:4202, 1987), wherein replacement of the phosphorus linkage by short homopolymers containing carbamate or morpholino linkages is limited by methodology, the solubility of the resulting molecule, and hybridization properties; Mazur (*Tetrahedron* 40:3949, 1984), wherein replacement of the phosphorus linkage with a phosphonic linkage has not been developed beyond the synthesis of a homotrimer molecule; and Goodrich (*Bioconj. Chem.* 1:165, 1990) wherein ester linkages are enzymatically degraded by esterases and are therefore unsuitable to replace the phosphonate bond in antisense applications.

Another key factor are the sterochemical effects of that arise in oligomers having chiral centers. In general, an oligomer with a length of n nucleosides will constitute a mixture of $2^{n-1}$ isomers in successive non-stereospecific chain synthesis.

It has been observed that Rp and Sp homochiral chains, whose absolute configuration at all internucleotide methanephosphonate phosphorus atoms is either Rp or Sp, and non-stereoregular chains show different physicochemical properties as well as different capabilities of forming adducts with oligonucleotides of complementary sequence. In addition, phosphorothioate analogs of nucleotides have shown substantial stereoselectivity differences between Oligo-Rp and Oligo-Sp oligonucleotides in resistance to nucleases activity (Potter, *Biochemistry*, 22:1369, 1983; Bryant et al., *Biochemistry*, 18:2825, 1979).

Lesnikowski (*Nucl. Acids Res.*, 18:2109, 1990 observed that diastereomeric pure octathymidine methanephosphonates, in which six out of seven methanephosphonate bonds have defined configuration at the phosphorus atom when complexed with a the matrix of pentadecadeoxyriboadenylic acid show substantial differences in melting temperatures. The Oligonucleotide compounds with predetermined configuration at the phosphorus atom, used in these studies, were prepared by the stereocontrolled process between the 5'-hydroxyl nucleoside group activated by means of the Grignard's reagent, and the diastereomerically pure nucleoside p-nitrophenylmethanephosphonate (Lesnikowski et al., *Nucl. Acids Res.*, 18:2109, 1990; Lesnikowski et al., *Nucleosides & Nucleotides*, 10:773, 1991; Lesnikowski, *Nucl. Acids Res.*, 16:11675, 1988). This method, however, requires long reaction time, and has been verified only in the case of the synthesis of tetramer homothymidine fragments and heteromeric hexamers.

Attempts to prepare diastereomerically pure oligomethylphosphonate compounds by reacting at low temperatures (−80° C.) with methyldichlorophosphine and appropriate nucleosides protected at 5' or 3' positions, resulted in the formation of Rp isomers of relevant dinucleoside methylphosphonates at a maximum predominace of 8:1 (Loeschner, *Tetrahedron Lett.*, 30:5587, 1989; and Engels et al., *Nucleosides & Nucleotides*, 10:347, 1991).

However, longer stereoregular chains cannot be prepared by this method because intermediate nucleoside 3'-O-chloromethylphosphonites, formed during the condensation, have a labile configuration even at low temperatures.

The limitations of the available methods for modification and synthesis of the organophosphorus derivatives have led to a continuing and long felt need for other modifications which provide resistance to nucleases and satisfactory hybridization properties for antisense oligonucleotide diagnostics, therapeutics, and research.

SUMMARY OF THE INVENTION

According to one aspect of the present invention, compositions of novel monomeric organophosphorus derivatives are provided. A first series of compounds is provided having the structure of formula (1) wherein (a) Y is a primary amine moiety, an S-aryl moiety, an Se-aryl moiety, an S-haloalkyl moiety, or an Se-haloalkyl moiety of 1 to about 10 carbon atoms, or $X_1R_3$, wherein $X_1$ is O, S, or Se, and $R_3$ is an aralkyl moiety, a haloaryl moiety, or an alkaryl moiety of 6 to about 20 carbon atoms, or an aromatic heterocyclic moiety of 5 to 10 carbon atoms; (b) Z is an aralkyl moiety, a haloalkyl moiety, an alkenyl moiety, an alkynyl moiety, or an alkaryl moiety of 1 to about 20 carbon atoms, an aminomethyl, or an aminoethyl; (c) $R_1$ is a protecting group; (d) $R_2$ is H, a halogen, an alkyl moiety of 1 to about 20 carbon atoms, an alkaryl moiety or an aralkyl moiety of about 5 to about 20 carbon atoms, CN, $N_3$, a protected NH2, $CF_3$, $OCF_3$, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, an O-aryl moiety, an S-aryl moiety, an N-aryl moiety, or $O(R_4)$, wherein $R_4$ is a protecting group; and (e) B is an optionally protected nucleoside base.

A second series of compounds is provided having the structure of formula (1) wherein (a) Y is an amine moiety, a halogen, or $X_1R_3$, wherein $X_1$ is O, S, or Se, and $R_3$ is an alkyl moiety, an aralkyl moiety, a haloalkyl moiety, a haloaryl moiety, an alkaryl moiety, or an aryl moiety of 1 to about 20 carbon atoms, or an aromatic heterocyclic moiety of 5 to 10 carbon atoms; (b) Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; (c) $R_1$ is a protecting group; (d) $R_2$ is H, a halogen, an alkyl moiety of 1 to about 20 carbon atoms, an alkaryl moiety or an aralkyl moiety of about 5 to about 20 carbon atoms, CN, $N_3$, a protected $NH_2$, $CF_3$, $OCF_3$, an O-alkyl moiety, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, an O-aryl moiety, an S-aryl moiety, an N-aryl moiety, or $O(R_4)$, wherein $R_4$ is a protecting group; and (e) B is an optionally protected nucleoside base.

A third series of compounds is provided having structure of formula (1) wherein (a) Y is a primary amine, a halogen, or $X_1R_3$, wherein $X_1$ is O, S, or Se, and $R_3$ is an alkyl moiety, an aralkyl moiety, a haloalkyl moiety, a haloaryl moiety, an alkaryl moiety, or an aryl moiety of 1 to about 20 carbon atoms, or a aromatic heterocyclic moiety of 5 to 10 carbon atoms; (b) Z is an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; (c) $R_1$ is a protecting group; (d) $R_2$ is a halogen, an alkyl moiety of 1 to about 20 carbon atoms, an alkaryl moiety or an aralkyl moiety of about 5 to about 20 carbon atoms, CN, $N_3$, a protected $NH_2$, $CF_3$, $OCF_3$, an O-alkyl moiety, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, an O-aryl moiety, an S-aryl moiety, an N-aryl moiety, or $O(R_4)$, wherein $R_4$ is a protecting group; and (e) B is an optionally protected nucleoside base.

A fourth series of compounds is provided having the structure of formula (1) wherein (a) Y is a primary amine moiety, an O-aralkyl, an S-aryl moiety, a Se-aryl moiety, an S-haloalkyl moiety, a Se-haloalkyl moiety, a branched O-alkyl moiety of 3 to about 10 carbon atoms, or $X_1R_3$, wherein $X_1$ is O, S, or Se, and $R_3$ is an aralkyl moiety, a haloaryl moiety, or an alkaryl moiety of 1 to about 20 carbon atoms, or a aromatic heterocyclic moiety of 5 to 10 carbon atoms; (b) Z is an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; (c) $R_1$ is a protecting group; (d) $R_2$ is a halogen, an alkyl moiety of 1 to about 20 carbon atoms, an alkaryl moiety or an aralkyl moiety of about 5 to about 20 carbon atoms, CN, $N_3$, protected $NH_2$, $CF_3$, $OCF_3$, an O-alkyl moiety, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, O-aryl moiety, S-aryl moiety, an N-aryl moiety, or $O(R_4)$, wherein $R_4$ is a protecting group; and (e) B is an optionally protected nucleoside base.

It is preferable that when Y is a primary amine moiety the amine is $NHR_5$ wherein $R_5$ is a straight chain or branched alkyl moiety, aralkyl moiety, aryl moiety, or alkaryl moiety of 1 to about 20 carbon atoms, a cycloalkyl moiety of 3 to about 8 carbon atoms, or a polycycloalkyl moiety of about 10 to about 30 carbon atoms.

It is further preferred that $R_3$ is $CH_3$ or $CH_2C_6H_4R_6$ wherein $R_6$ is H, a straight chain or a branched alkyl moiety of 1 to about 6 carbon atoms, a straight chain or a branched haloalkyl moiety of 1 to about 6 carbon atoms, a halogen, or $NO_2$ in the second and third series of compounds above. Alternatively, it is preferable that $R_3$ is $CH_2C_6H_4R_6$ wherein $R_6$ is H, a straight chain or a branched alkyl moiety of 1 to about 6 carbon atoms, a straight chain or a branched haloalkyl moiety of 1 to about 6 carbon atoms, a halogen, or $NO_2$ in the first and forth series of compounds above.

In another aspect of the present invention dimeric organophosphorus derivatives are provided. In one embodiment of this aspect of the invention a compound having the structure of formula (3) wherein (a) X is O or S; (b) Z is an alkyl moiety of about 4 to about 20 carbon atoms, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; (c) $R_1$ is a protecting group; (d) $R_2$ is an alkyl moiety of 1 to about 20 carbon atoms, an alkaryl moiety or an aralkyl moiety of about 5 to about 20 carbon atoms, CN, $N_3$, $NH_2$, $CF_3$, $OCF_3$, a S-alkyl moiety, an N-alkyl moiety, an S-alkenyl moiety, an N-alkenyl moiety, an O-alkynyl moiety, an S-alkynyl moiety, an N-alkynyl moiety, an O-aryl moiety, an S-aryl moiety, or an N-aryl moiety; (e) $R_9$ is an acyl protecting group, a coupling group, or a silyl protecting group; and (f) B is an optionally protected nucleoside base.

In still another aspect of the invention methods are provided for the synthesis of organophosphorus mononucleoside derivatives. In one embodiment of the invention a method for the synthesis of any of the series of compounds is provided comprising the steps of;

(a) reacting a Z-substituted dichlorophosphine in the presence of a hydrogen chloride scavenger and a nucleoside of formula (2) wherein $R_1$ is a protecting group, $R_2$ is H or an alkoxide moiety of 1 to about 10 carbon atoms, and B is an N-protected nucleoside base, and (b) adding aniline and sulfur or selenium or an oxidizing agent to the reaction mixture to produce a mixture of diastereomers of 3'-O-(Z-substituted) phosphonoanilidothioates, 3'-O-(Z-substituted) phosphonoanilidoselenoates, or 3'-O-(Z-substituted) phosphonoanilidates. In a prefered embodiment, the oxidizing agent is selected from the group consisting of iodine/2,6-lutidine/$H_2O$, t-butylhydroperoxide, or (±)-(10-camphorsulfonyl)oxaziridine.

In another embodiment of the invention, a method for the synthesis of a compound according to the first and fourth series of compounds above is provided wherein Y is $X_1R_3$, wherein $X_1$ is S or Se and $R_3$ is $CH_2C_6H_4R_7$, wherein $R_7$ is H, Cl, or $NO_2$, comprising the steps of;

(a) reacting a Z-substituted dichlorophosphine in the presence of a hydrogen chloride scavenger and a nucleoside of the formula (2) wherein $R_1$ is a protecting group, $R_2$ is H or an alkoxide moiety of 1 to about 10 carbon atoms, and B is an N-protected nucleoside base, (b) adding aniline and sulfur or selenium to the reaction mixture to produce a mixture of diastereomers of 3-O-(Z-substituted)phosphonoanilidothioates, or 3'-O-(Z-substituted)phosphonoanilidoselenoates, (c) reacting the mixture of diastereomers from step (b) with sodium hydride or with 1,8-diazabicyclo[5.4.0] undec-7-ene, (DBU), and carbon dioxide to produce transient nucleoside (Z-substituted)phosphonothioic acids, or (Z-substituted) phosphonoselenoic acids; and (d) alkylating the transient nucleosides of step (c) by treatment with an alkylating agent of the formula $R_8W$, wherein $R_8$ is $CH_2C_6H_4R_7$, wherein $R_7$ is H, Cl, or $NO_2$ and W is Cl, Br, or I.

In yet another embodiment a method for the synthesis of a compound the first and fourth series of compounds above is provided comprising the steps of;

(a) reacting Z-substituted dichlorophosphine in the presence of a hydrogen chloride scavenger and a nucleoside of the formula (2) wherein $R_1$ is a protecting group, $R_2$ is H or an alkoxide moiety of 1 to about 10 carbon atoms and B is an N-protected nucleoside base, (b) adding aniline and sulfur or selenium to the reaction to produce a mixture of diastereomers of 3'-O-(Z-substituted)phosphonoanilidothioate, or 3'-O-(Z-substituted)phosphonoanilidoselenoate, and (c) oxidizing the mixture of diastereomers by treatment with an oxidizing agent.

In still another embodiment a method for the synthesis of a compound of the first and fourth series of compounds above is provided wherein Y is $X_1R_3$ wherein $X_1$ is S and $R_3$ is —$CH_2C_6H_4R_7$, wherein $R_7$ is H, Cl, or $NO_2$, comprising the steps of:

(a) reacting Z-substituted dichlorophosphine in the presence of a hydrogen chloride scavenger and a nucleoside of the formula (2) wherein $R_1$ is a protecting group, $R_2$ is H or an alkoxide moiety of 1 to about 10 carbon atoms and B is an N-protected nucleoside base, (b) adding aniline and sulfur or selenium to the reaction to produce a mixture of diastereomers of 3'-O-(Z-substituted)phosphonoanilidothioates, or 3'-O-(Z-substituted)phosphonoanilidoselenoates, (c) oxidizing the mixture of diastereomers by treatment with an oxidizing agent to give oxidized diastereomers, (d) reacting the oxidized diastereomers from step (c) with sodium hydride or with 1,8-diazabicyclo[5.4.0]undec-7-ene and carbon disulfide to produce a transient nucleoside 3'-O-(Z-substituted)phosphonothioic acid, and (e) alkylating the transient nucleoside 3'-O-(Z-substituted)phosphonothioic acid by treatment with an alkylating agent of the general formula $R_8Z$, wherein $R_8$ is —$CH_2C_6H_4R_7$, wherein $R_7$ is H, Cl, or $NO_2$, and Z is Cl, Br, or I.

It is preferable that the $R_1$ protecting is methoxymethyl ether, methoxyethoxymethyl ether, 2(-trimethylsilyl)ethoxy ether, acyl, carbamoyl, substituted silyl, 4,4'-dimethoxytrityl, or 9-phenylxanthene-9-oxyl.

It is further preferred that the hydrogen chloride scavenger be triethylamine, diisopropylethylamine, pyridine, or any tertiary alkyl or aryl amine.

In addition it is preferred that the oxidizing agent be potassium peroxymonosulfate or hydrogen peroxide.

In another aspect of the invention, methods are provided for the synthesis of organophosphorus derivative dinucleosides utilizing the monomeric organophosphorus derivatives provided above. In one embodiment a method for the synthesis of a diastereomeric mixture of P-chiral dinucleosides of formulas (6a) and (6b) is provided wherein $R_1$ is a protecting group; $R_2$ is H or alkoxy moiety of 1 to about 10 carbon atoms; $R_9$ is acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and B is an N-protected nucleoside base comprising the steps of;

(a) reacting nucleosides of formulas (8a) and (8b) with sodium hydride or 1,8-diazabicyclo[5.4.0]undec-7-ene and carbon dioxide to form transient nucleoside 3'-O-(Z-substituted)phosphonothioic acids, (b) reacting the transient nucleosides with an alkylating agent of the formula $R_8W$, wherein $R_8$ is $CH_2C_6H_4R_7$, wherein $R_7$ is H, Cl, or $NO_2$, and W is Cl, Br, or I, to form nucleoside intermediates of formulas (7a) and (7b), and (c) reacting the nucleoside intermediates with a nucleoside of the formula (5) in presence of an activator and a lithium salt in an aprotic organic solvent to form the diastereomeric mixture of P-chiral dinucleosides.

In another embodiment a method for the synthesis of a diastereomeric mixture of P-chiral dinucleosides of formulas (6a) and (6b) is provided wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and B is an N-protected nucleoside base comprising the steps of;

(a) reacting nucleosides of formulas (10a) and (10b) with sodium hydride or 1,8-diazabicyclo[5.4.0]undec-7-ene and carbon dioxide to form transient nucleoside 3'-O-(Z-substituted)phosphonoselenoic acids, (b) reacting the transient nucleosides of step (a) with an alkylating agent of the formula $R_8W$, wherein $R_8$ is $CH_2C_6H_4R_7$, wherein $R_7$ is H, Cl, or $NO_2$, and W is Cl, Br, or I, to form nucleoside intermediates of formulas (11a) and (11b), and (c) reacting the nucleoside intermediate with a nucleoside of the formula (5) in presence of an activator and a lithium salt in an aprotic organic solvent to form the diastereomeric mixture of P-chiral dinucleosides.

In still another embodiment, a method for the synthesis of a diastereomeric mixture of P-chiral dinucleosides of formulas (6a) and (6b) is provided wherein $R_1$ is a protecting group; $R_2$ is H, OH, or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety or an atoms, an aminomethyl, or an aminoethyl; and B is an N-protected nucleoside base comprising the steps of;

(a) reacting nucleosides of formulas (8a) and (8b) with potassium peroxymonosulfate or hydrogen peroxide to form intermediate nucleosides of formulas (9a) and (9b), (b) reacting the intermediate nucleosides from step (a) with sodium hydride or DBU and carbon disulfide to form transient nucleoside 3'-O-(Z-substituted) phosphonothioic acids, (c) reacting the transient nucleosides with an alkylating agent of the formula $R_8W$, wherein $R_8$ is $CH_2C_6H_4R_7$, wherein $R_7$ is H, Cl, or $NO_2$, and W is Cl, Br, or I, to form nucleoside intermediates of formulas (7a) and (7b), and (d) reacting the nucleoside intermediates from step (c) with a nucleoside of formula (5) in presence of an activator and a lithium salt in an aprotic organic solvent to form a diastereomeric mixture of P-chiral dinucleosides.

In still another embodiment of the invention, a method for the synthesis of a diastereomeric mixture of P-chiral dinucleosides of formulas (6a) and (6b) is provided wherein $R_1$ is a protecting group; $R_2$ is H, OH, or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety or an alkaryl moiety, or an aryl moiety of 1 to about 20 carbon atoms, an aminomethyl, or an aminoethyl; and B is an N-protected nucleoside base comprising the steps of;

(a) reacting nucleosides of formulas (10a) and (10b) with potassium peroxymonosulfate or hydrogen peroxide to form the intermediate nucleosides of formulas (9a) and (9b), and (b) reacting intermediate nucleosides from step (a) with sodium hydride or DBU and carbon diselenide to form transient nucleoside 3'-O-(Z-substituted) phosphonoselenoic acids, (c) reacting the transient nucleosides from step (b) with an alkylating agent of the formula $R_8W$, wherein $R_8$ is $CH_2C_6H_4R_7$, wherein $R_7$ is H, Cl, or $NO_2$, and W is Cl, Br, or I, to form nucleoside intermediates of formulas (9a) and (9b), (d) reacting the nucleoside intermediates of step (c) with a nucleoside of the formula (5) in presence of an activator and a lithium salt in an aprotic organic solvent to form a diastereomeric mixture of P-chiral dinucleosides.

In another aspect of this invention, methods for the synthesis of chirally pure organophosphorus derivative dinucleotides is provided. In one embodiment of this aspect of the invention a method for the synthesis a chirally pure dinucleoside of formula (6a) is provided wherein $R_1$ is a protecting group; $R_2$ is H, OH, or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and B is an N-protected nucleoside base comprising the steps of;

(a) reacting a nucleoside of formula (8a) with sodium hydride or 1,8-diazabicyclo[5.4.0]undec-7-ene and carbon dioxide to form a transient nucleoside 3'-O-(Z-substituted)phosphonothioic acid, (b) reacting the transient nucleoside of step (a) with an alkylating agent of the formula $R_8W$, wherein $R_8$ is $CH_2C_6H_4R_7$, wherein $R_7$ is H, Cl, or $NO_2$, and W is Cl, Br, or I, to form a nucleoside intermediate of formula (7a), and (c) reacting the nucleoside intermediate from step (b) with a nucleoside of formula (5) in presence of an activator and a lithium salt in an aprotic organic solvent to form a chirally pure dinucleoside.

In another embodiment of the invention, a method for the synthesis of a chirally pure dinucleoside of formula (6a) is provided wherein $R_1$ is a protecting group; $R_2$ is H, OH, or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and B is an N-protected nucleoside base comprising the steps of;

(a) reacting a nucleoside of formula (10a) with sodium hydride or 1,8-diazabicyclo[5.4.0]undec-7-ene and carbon dioxide to form a transient nucleoside 3'-O-(Z-substituted)phosphonoselenoic acid, (b) reacting the transient nucleoside from step (a) with an alkylating agent of the formula $R_8W$, wherein $R_8$ is $CH_2C_6H_4R_7$, wherein $R_7$ is H, Cl, or $NO_2$, and W is Cl, Br, or I, to form a nucleoside intermediate of formula (11a), and (c) reacting the nucleoside intermediate from step (b) with a nucleoside of the formula (5) in presence of an activator and a lithium salt in an aprotic organic solvent to form a chirally pure dinucleoside.

In still another embodiment, a method for the synthesis of a chirally pure dinucleoside of formula (6a) is provided wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and (e) B is an N-protected nucleoside base comprising the steps of;

(a) reacting a nucleoside of formula (8b) with potassium peroxymonosulfate or hydrogen peroxide to form a intermediate nucleoside of formula (9b), (b) reacting the intermediate nucleoside from step (a) with sodium hydride or DBU and carbon disulfide to form a transient nucleoside 3'-O-(Z-substituted) phosphonothioic acid, (c) reacting the transient nucleoside from step (b) with an alkylating agent of the formula $R_8W$, wherein $R_8$ is $CH_2C_6H_4R_7$, wherein $R_7$ is H, Cl, or $NO_2$, and W is Cl, Br, or I, to form a alkylated nucleoside of formula (7a), (d) reacting the alkylated nucleoside from step (c) with a nucleoside of the formula (5) in presence of an activator and a lithium salt in an aprotic organic solvent to form the chirally pure dinucleoside.

In yet another embodiment of the invention, a method for the synthesis a chirally pure dinucleoside of formula (6a) is provided wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and (e) B is an N-protected nucleoside base comprising the steps of;

(a) reacting a nucleoside of formula (10b) with potassium peroxymonosulfate or hydrogen peroxide to form a intermediate nucleoside of formula (9b), (b) reacting the intermediate nucleoside from step (a) with sodium hydride or DBU and carbon diselenide to form transient nucleoside 3'-O-(Z-substituted) phosphonoselenoic acids, (c) reacting the transient nucleoside from step (b) with an alkylating agent of the formula $R_8W$, wherein $R_8$ is $CH_2C_6H_4R_7$, wherein $R_7$ is H, Cl, or $NO_2$, and W is Cl, Br, or I, to form a alkylated nucleoside of formula (11a), and (d) reacting the alkylated nucleoside from step (c) with a nucleoside of formula (5) in presence of an activator and a lithium salt in an aprotic organic solvent to form a chirally pure dinucleoside.

In still another embodiment, a method for the synthesis a chirally pure dinucleoside of the formula (6b) is provided wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl or an aminoethyl; and (e) B is an N-protected nucleoside base comprising the steps of;

(a) reacting a nucleoside of formula (8b) with sodium hydride or DBU and carbon dioxide to form a transient nucleoside 3'-O-(Z-substituted)phosphonothioic acid, (b) reacting the transient nucleoside from step (a) with an alkylating agent of the formula $R_8W$, wherein $R_8$ is $CH_2C_6H_4R_7$, wherein $R_7$ is H, Cl, or $NO_2$, and W is Cl, Br, or I, to form an alkylated nucleoside of the formula (7b), and (c) reacting the alkylated nucleoside from step (b) with a nucleoside of formula (5) in presence of an activator and a lithium salt in an aprotic organic solvent to form a chirally pure dinucleoside.

In yet another embodiment, a method for the synthesis a chirally pure dinucleoside of formula (6b) is provided wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and (e) B is an N-protected nucleoside base comprising the steps of;

(a) reacting a nucleoside of formula (10b) with sodium hydride or DBU and carbon dioxide to form a transient nucleoside 3'-O-(Z-substituted)phosphonoselenoic acid, (b) reacting the transient nucleoside from step (a) with an alkylating agent of the formula $R_8W$, wherein $R_8$ is $CH_2C_6H_4R_7$, wherein $R_7$ is H, Cl, or $NO_2$, and W is Cl, Br, or I, to form an alkylated nucleoside of formula (11b), and (c) reacting the alkylated nucleoside from step (b) with a nucleoside of formula (5) in presence of an activator and a lithium salt in an aprotic organic solvent to form a chirally pure dinucleoside.

In still another embodiment, a method for the synthesis a chirally pure dinucleoside of formula (6b) is provided wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and B is an N-protected nucleoside base comprising the steps of;

(a) reacting a nucleoside of formula (8a) with potassium peroxymonosulfate or hydrogen peroxide to form an intermediate nucleoside of formula (9a), (b) reacting the intermediate nucleoside from step (a) with sodium hydride or DBU and carbon disulfide to form the transient nucleoside 3'-O-(Z-substituted) phosphonothioic acid, (c) reacting the transient nucleoside from step (b) with an alkylating agent of the formula $R_8W$, wherein $R_8$ is $CH_2C_6H_4R_7$, wherein $R_7$ is H, Cl, or $NO_2$, and W is Cl, Br, or I, to form an alkylated nucleoside intermediate of formula (7b), and (d) reacting the alkylated intermediate from step (c) nucleoside with a nucleoside of formula (5) in presence of an activator and a lithium salt in an aprotic organic solvent to form the chirally pure dinucleosides.

In still another embodiment, a method for the synthesis a chirally pure dinucleoside of formula (6b) is provided wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and B is an N-protected nucleoside base comprising the steps of;

(a) reacting a nucleoside of formula (10a) with potassium peroxymonosulfate or hydrogen peroxide to form a intermediate nucleoside of formula (9a), (b) reacting the intermediate nucleoside from step (a) with sodium hydride or DBU and carbon diselenide to form the transient nucleoside 3'-O-(Z-substituted) phosphonoselenoic acid, (c) reacting the transient nucleoside from step (b) with an alkylating agent of the formula $R_8W$, wherein $R_8$ is $CH_2C_6H_4R_7$, wherein $R_7$ is H, Cl, or $NO_2$, and W is Cl, Br, or I, to form an alkylated nucleoside intermediate of formula (11b), and (d) reacting the alkylated nucleoside intermediate of step (c) with a nucleoside of the formula (5) in presence of an activator and a lithium salt in an aprotic organic solvent to form the chirally pure dinucleosides.

It is preferred that the aprotic organic solvent is acetonitrile, and the activator be 1,8-diazabicyclo [5.4.0] undec-7-ene.

DETAILED DESCRIPTION

Figure 1:
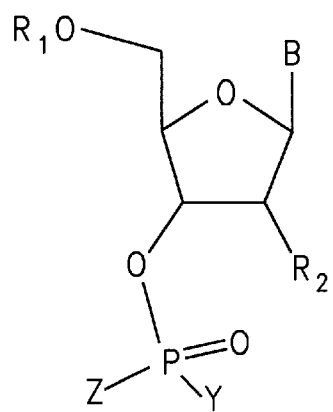
FIG. 1 depicts chemical structure of an organophosphorous mononucleoside derivative of formula (1).
Figure 2:
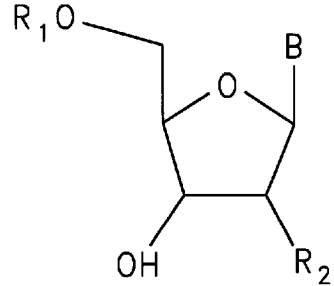
FIG. 2 depicts the chemical structure of an organophosphorous mononucleoside derivative of formula (2).
Figure 3:
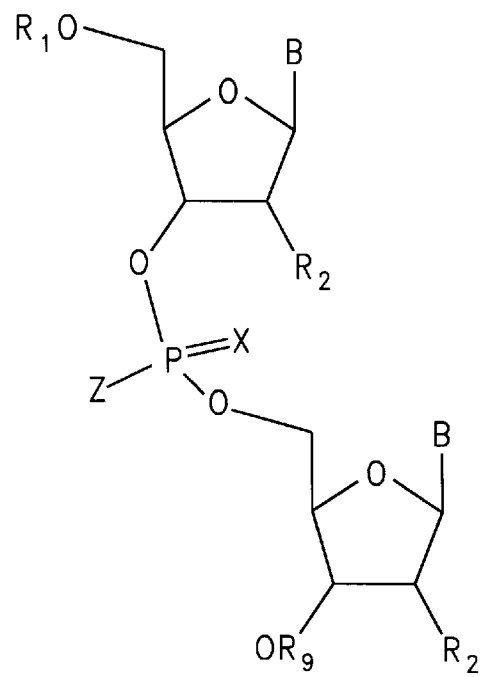
FIG. 3 depicts the chemical structure of an organophosphorous dinucleoside derivative of formula (3).
Figure 4:
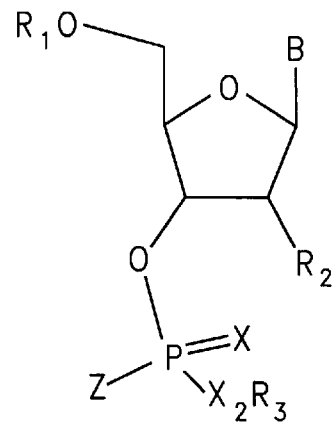
FIG. 4 depicts the chemical structure of an organophosphorous mononucleoside derivative of formula (4).
Figure 5:
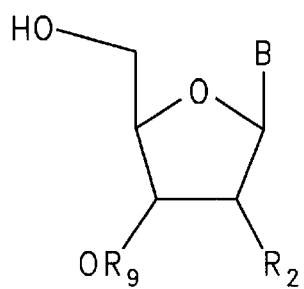
FIG. 5 depicts the chemical structure of an organophosphorous mononucleoside derivative of formula (5).
Figure 6A:
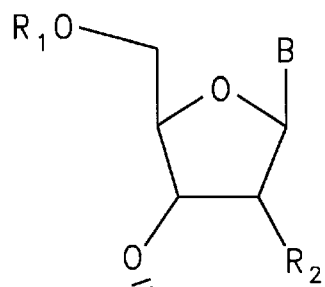
FIG. 6 depicts the chemical structures of diastereomeric organophosphorous dinucleoside derivatives of formula (6a) and (6b).
Figure 6B:
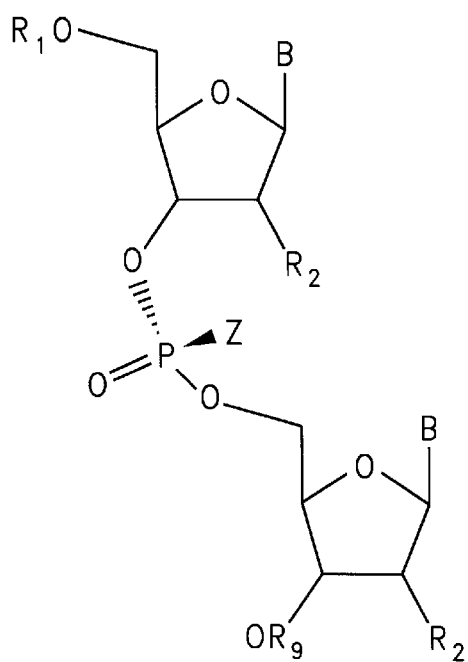
Figure 7A:
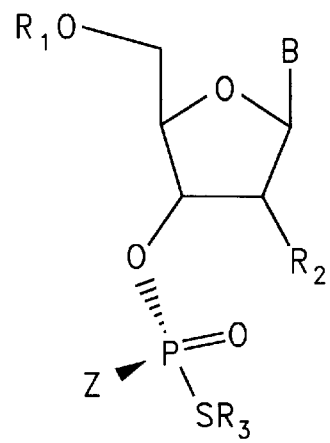
FIG. 7 depicts the chemical structures of diastereomeric organophosphorous dinucleoside derivatives of formula (7a) and (7b).
Figure 7B:
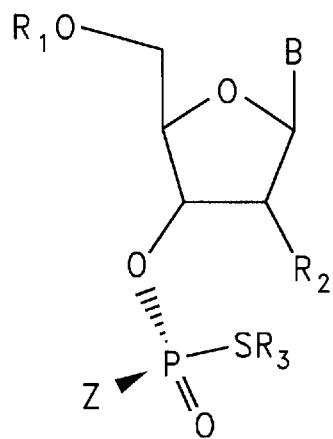
Figure 8A:
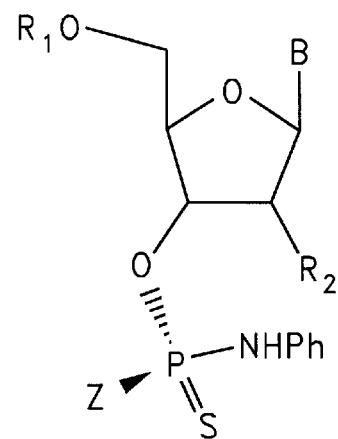
FIG. 8 depicts the chemical structures of diastereomeric organophosphorous dinucleoside derivatives of formula (8a) and (8b).
Figure 8B:
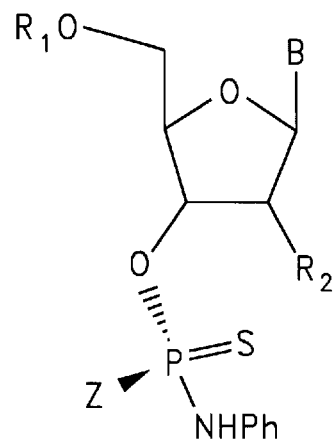
Figure 9A:
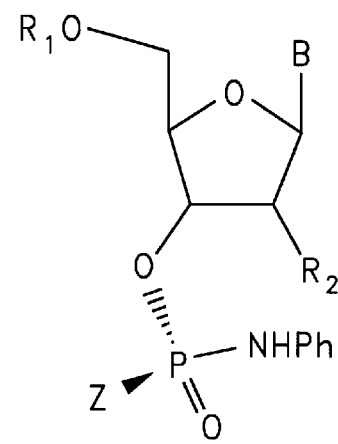
FIG. 9 depicts the chemical structures of diastereomeric organophosphorous dinucleoside derivatives of formula (9a) and (9b).
Figure 9B:
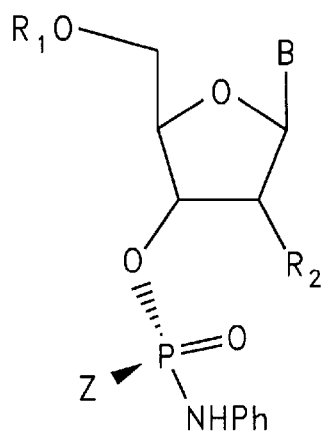
Figure 10A:
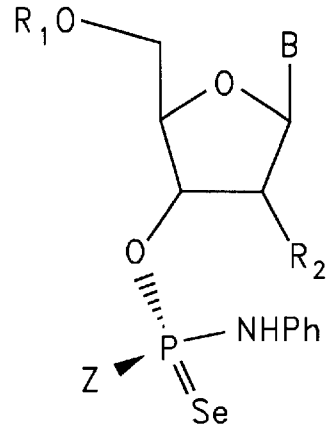
FIG. 10 depicts the chemical structures of diastereomeric organophosphorous dinucleoside derivatives of formula (10a) and (10b).
Figure 10B:
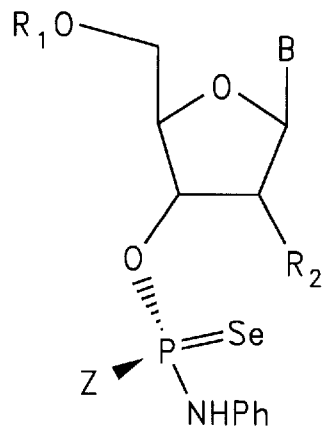
Figure 11A:
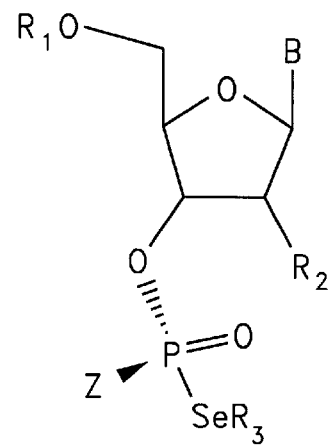
FIG. 11 depicts the chemical structures of diastereomeric organophosphorous dinucleoside derivatives of formula (11a) and (11b).
Figure 11B:
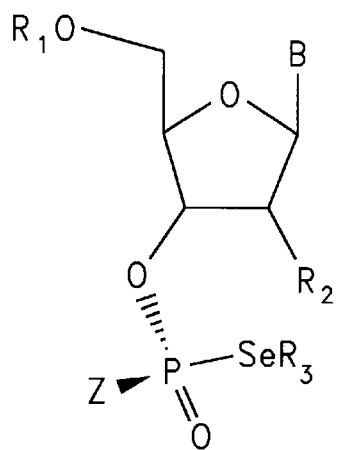
Figure 12:
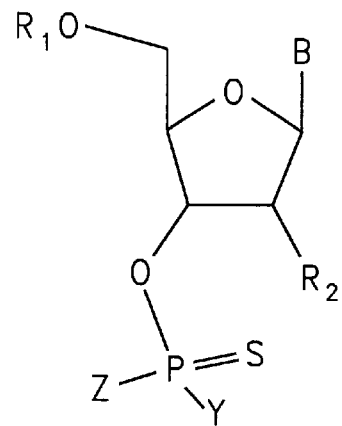
FIG. 12 depicts the chemical structure of an organophosphorous dinucleoside derivative of formula (12).
Figure 13:
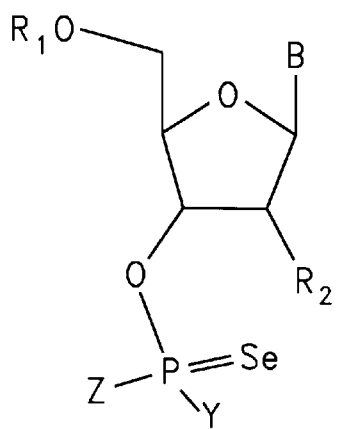
FIG. 13 depicts the chemical structure of an organophosphorous dinucleoside derivative of formula (13).
Figure 14:
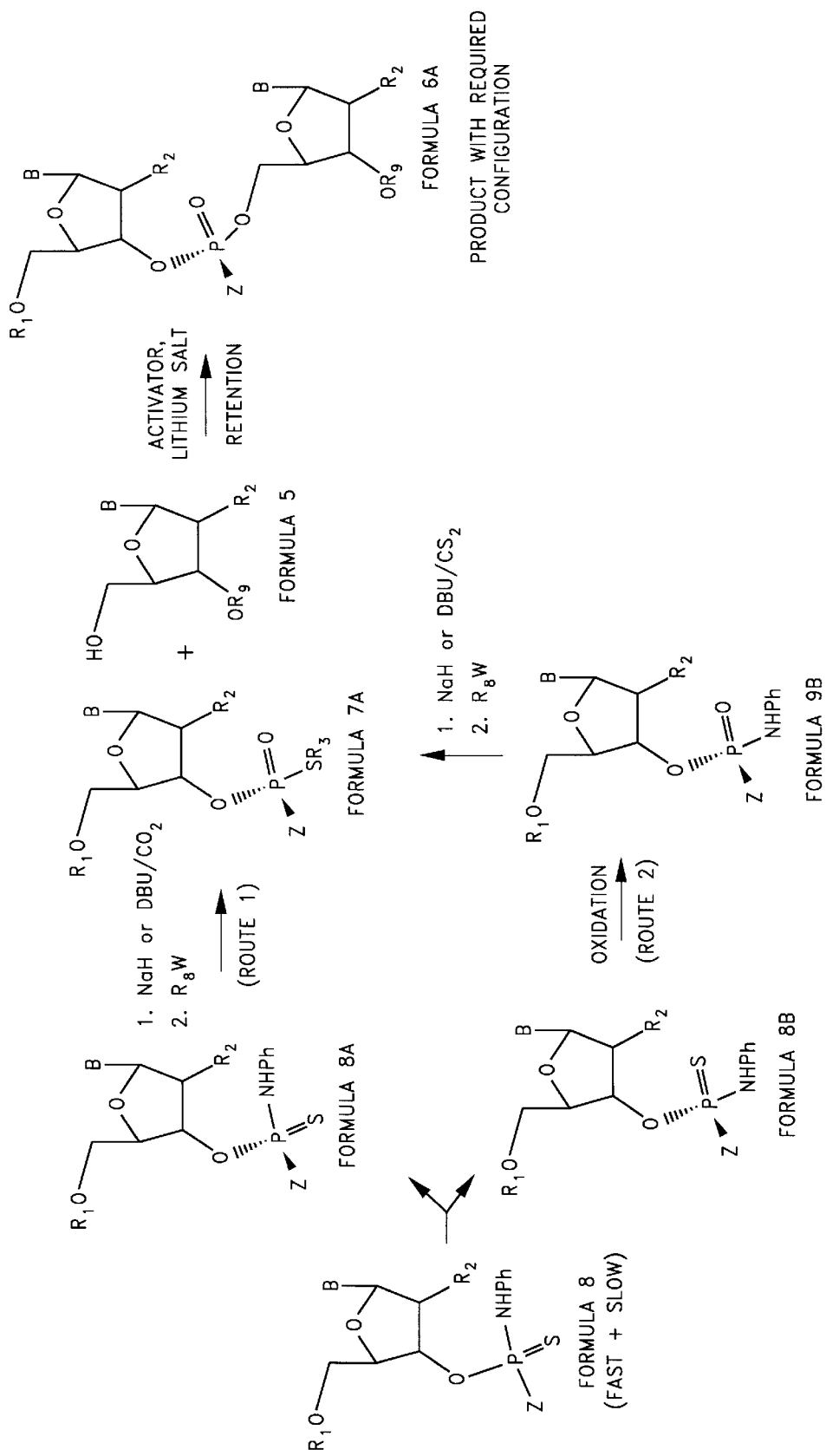
FIG. 14 depicts a reaction scheme for a method for the synthesis of an organophosphorus dinucleotide of formula (6a) from diastereomeric organophosphorus derivatives (8a) and (8b).
Figure 15:
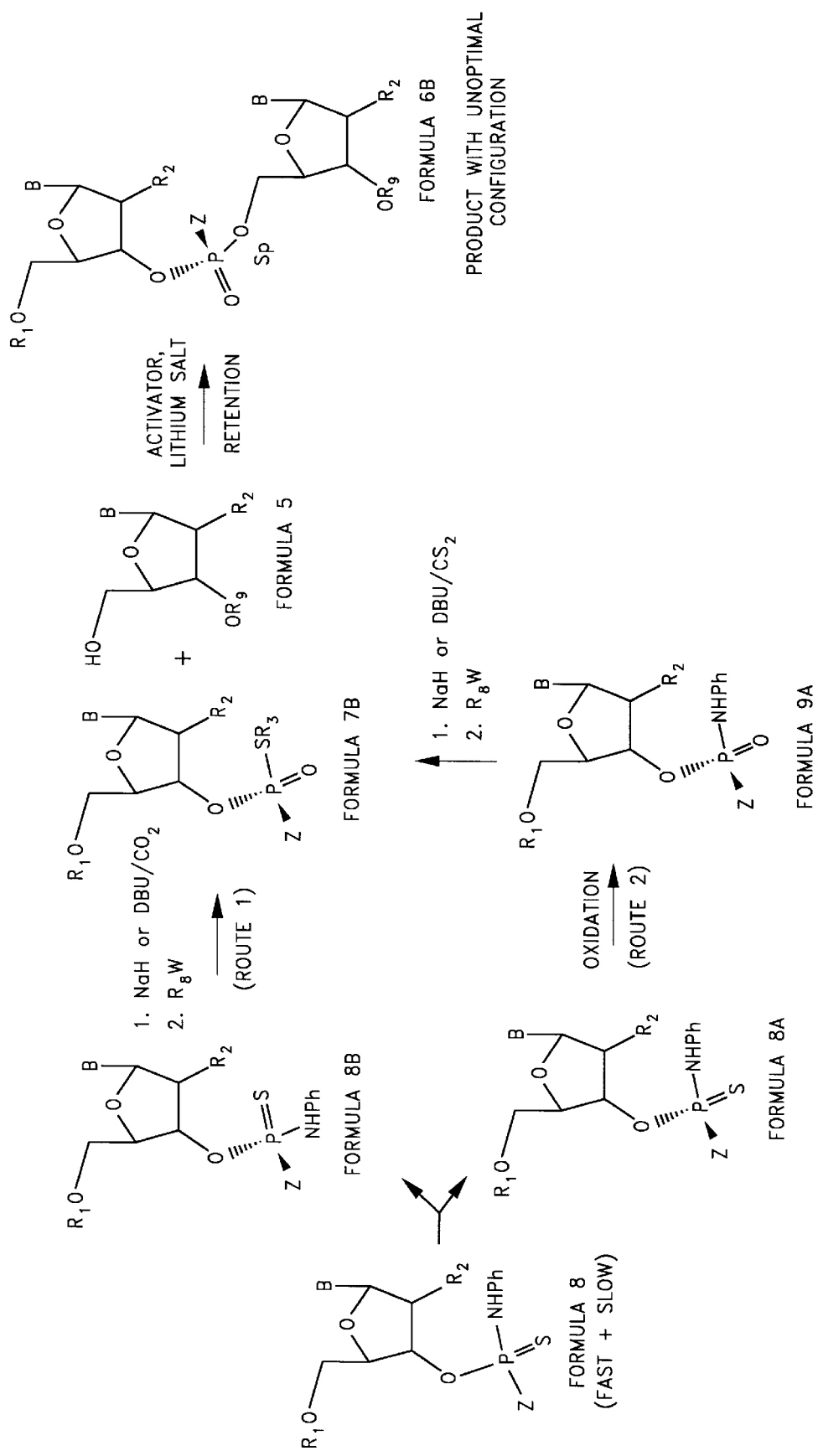
FIG. 15 depicts a reaction scheme for a method for the synthesis of an organophosphorus dinucleotide of formula (6b) from diastereomeric organophosphorus derivatives (8a) and (8b).
Figure 16:
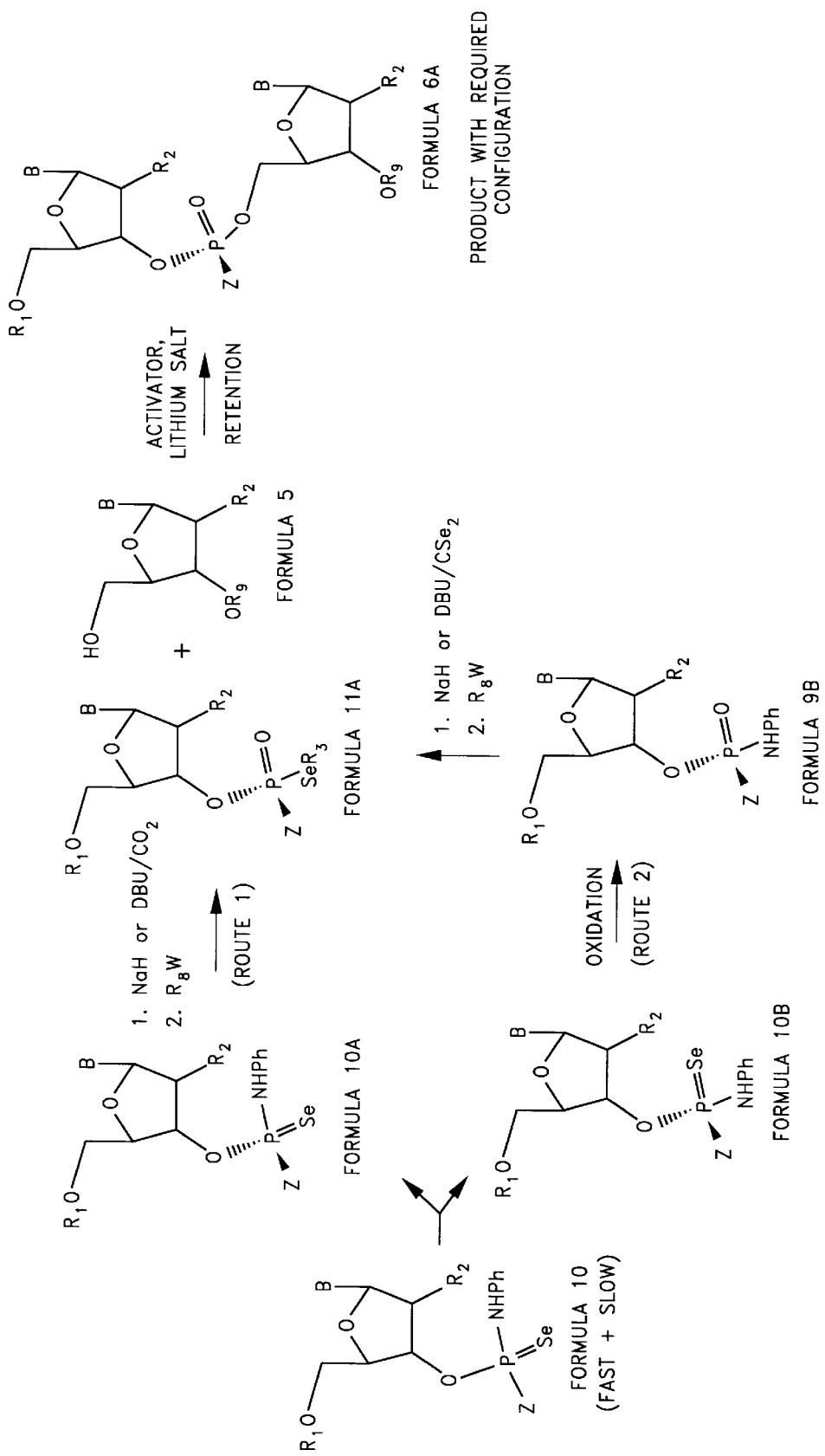
FIG. 16 depicts a reaction scheme for a method for the synthesis of an organophosphorus dinucleotide of formula (6a) from diastereomeric organophosphorus derivatives (10a) and (10b).
Figure 17:
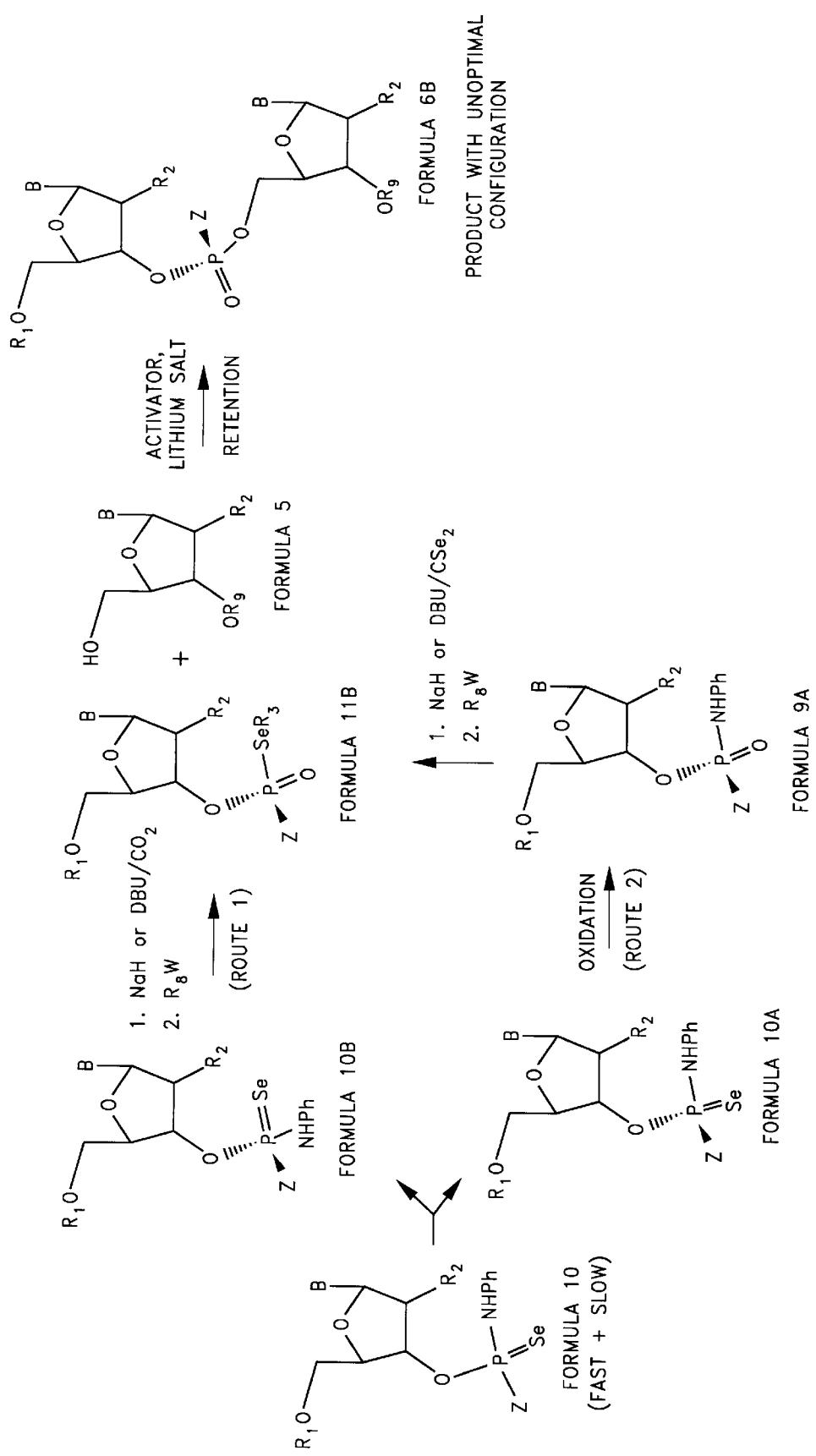
FIG. 17 depicts a reaction scheme for a method for the synthesis of organophosphorus dinucleotide of formula 6b from diastereomeric organophosphorus derivatives 10a and 10b.

Prior to setting forth the invention, it may be helpful to an understanding thereof to first set forth definitions of certain terms that will be used hereinafter. These terms have the following meaning unless expressly stated to the contrary.

The term "alkyl" refers to saturated aliphatic groups including straight-chain, branched-chain and cyclic groups. Suitable alkyl groups include cyclohexyl and cyclohexylmethyl. "Lower alkyl" refers to alkyl groups of 1 to 6 carbon atoms.

The term "aryl" refers to aromatic groups which have at least one ring having a conjugated pi electron system and includes carbocyclic aryl, heterocyclic aryl and biaryl groups, all of which may be optionally substituted.

The term "carbocyclic aryl" refers to aromatic groups wherein the ring atoms on the aromatic ring are carbon atoms. Carbocyclic aryl groups include monocyclic carbocyclic aryl groups and naphthyl groups, all of which may be optionally substituted. Suitable carboxyclic aryl grouyps include phenyl and naphthyl.

The term "aromatic heterocycle" refers to aromatic groups having from 1 to 3 heteroatoms as ring atoms in the aromatic ring and the remainder of the ring atoms are carbon atoms. Suitable heteroatoms include oxygen, sulfur, and nitrogen, and suitable heterocyclic aryls include furanyl, thienyl, poyridyl, pyrroilyl, pyrimidyl, pyrazinyl, imidazolyl, and the like.

The term "biaryl" refers to phenyl substituted by carbocyclic or heterocyclic aryl as defined herein, ortho, meta or para to the point of attachment of the phenyl ring, advantageously para.

The term "lower" referred to herein in connection with organic radicals or compounds defines such with up to and including 6, preferably up to and including 4 and advantageously one or two carbon atoms. Such groups may be straight chain or branched chain.

The term "alkoxy" refers to —OR wherein R is alkyl.

The term "aralkyl" refers to an alkyl group substituted with an aryl group. Suitable aralkyl groups include benzyl, picolyl, and the like, all of which may be optionally substituted.

The term "cycloalkyl" refers to a cyclic alkyl group. Suitable cycloalkyl groups include cyclohexyl.

The term "alkenyl" refers to an unsaturated aliphatic group having at least one double bond. The term "alkylene" refers to a divalent straing chain or branched chain saturated aliphatic radical.

The term "nucleoside base" refers to adenine, guanine, cytosine, thymidine, uracil as well as analogs and modified forms of naturally-occurring bases, including the pyrimidine-analogs such as pseudoisocytosine and pseudouracil, and other modified bases such as 8-substituted purines.

The term "Z-substituted" refers to a reagent or reactant which contains the Z substituent wherein Z is defined as aralkyl moiety, a haloalkyl moiety, an alkenyl moiety, an alkynyl moiety, or an alkaryl moiety of 1 to about 20 carbon atoms, an aminomethyl, or an aminoethyl and the reagent or reactant is that specified, for example, dichlorophosphine, phosphonothioic acid, phosphonoselenoic acid, phosphonoanilidoselenoate, or phosphonoanilidothioate.

The term "nucleoside" use in the terms "mononucleoside", "dinucleoside", and oligonucleoside refers to a subunit of a nucleic acid which comprises a 5-carbon sugar and a nitrogen-containing base. The term includes not only those nucleosidyl units having adenine, guanine, cytosine, thimidine and uracil, as their bases but also analogs and modified forms of naturally-occurring bases, including the pyrimidine analogs such as pseudoisocytosine and pseudouracil, and other modified bases such as 8-substituted purines. In RNA, the 5-carbon sugar is ribose; in DNA the 5-carbon sugar is deoxyribose. The term nucleoside also includes other analogs of such subunits, including those which have modified sugars such as 2'-O-alkyl ribose for example. The prefix of "mono", "di", and "oligo" refer to the number of nucleosides present. "Mono" means one and refers to a single nucleoside, "di" means two and refers to a compound comprising two nucleosides, and, "oligo" means many and refers to a compound with multiple nucleosides.

The limitations of the available methods for modification and synthesis of the organophosphorus derivatives have led to a continued need for other modifications which provide resistance to nucleases and satisfactory hybridization properties for antisense oligonucleotide diagnostics, therapeutics, and research. All references which have been cited below are hereby incorporated by reference in their entirety.

The organophosporus derivatives of this invention can be used in preparing oligonucleotides useful for diagnostics, therapeutics, as research reagents and for use in kits.

Chirally pure organophosphorus derivatives may be used in synthesizing oligonucleosides of preselected chirality, either enriched for $R_p$ configuration, $S_p$ configuration or a mixture thereof.

In particular, organophosphorus dinucleoside derivatives of the present invention of a defined chirality at the phosphonate may be coupled together using an automated DNA synthesizer. The dimer synthons have coupling groups which allow them to be coupled together to give a chirally enriched phosphonate oligomer (see Examples 5 to 13). From a stock of prepared organophosphorus dinucleoside derivatives, oligonucleosides of any nucleoside base sequence may be synthesized by linking together the appropriate dinucleosides. Dinucleosides are added to the growing oligonucleoside chain until an oligonucleoside having the desired number of nucleosides is obtained. The resulting oligonucleoside has a defined chirality at every other linkage.

Since the oligonucleotides thus produced may form duplexes or triple helix complexes or other forms of stable association with transcribed regions of nucleic acids, they may be used to interfere or inhibit or alter expression of a particular gene or target sequence in a living cell, allowing selective inactivation or inhibition or alteration of expression. The target sequence may be RNA, such as a pre-mRNA or an mRNA or DNA.

Many diseases and other conditions are characterized by the presence of undesired DNA or RNA, which may be in certain instances single stranded and in other instances double stranded. These diseases and conditions can be treated using the principles of antisense therapy as is generally understood in the art.

In accordance with the preferred embodiments, this invention is directed to organophosphorus mononucleoside and dinucleoside derivatives as well as methods for their synthesis. The mononucleosides of the present invention are characterized by formula (1)

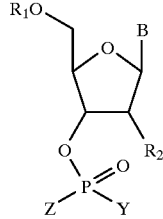

Formula 1 wherein

Y is a primary amine moiety, an S-aryl moiety, an Se-aryl moiety, an S-haloalkyl moiety, or an Se-haloalkyl moiety of 1 to about 10 carbon atoms, or $X_1R_3$, wherein $X_1$ is O, S, or Se, and $R_3$ is an aralkyl moiety, a haloaryl moiety, or an alkaryl moiety of 6 to about 20 carbon atoms, or an aromatic heterocyclic moiety of 5 to 10 carbon atoms;

Z is an aralkyl moiety, a haloalkyl moiety, an alkenyl moiety, an alkynyl moiety, or an alkaryl moiety of 1 to about 20 carbon atoms, an aminomethyl, or an aminoethyl;

$R_1$ is a protecting group;

$R_2$ is H, a halogen, an alkyl moiety of 1 to about 20 carbon atoms, an alkaryl moiety or an aralkyl moiety of about 5 to about 20 carbon atoms, CN, $N_3$, a protected $NH_2$, $CF_3$, $OCF_3$, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, an O-aryl moiety, an S-aryl moiety, an N-aryl moiety, or $O(R_4)$, wherein $R_4$ is a protecting group; and B is an optionally protected nucleotide base.

Another mononucleoside of the present invention is characterized by formula (1) wherein Z, $R_1$, and B are identical to that described above and Y is an amine moiety, a halogen, or $X_1R_3$, wherein $X_1$ is O, S, or Se, and $R_3$ is an alkyl moiety, an aralkyl moiety, a haloalkyl moiety, a haloaryl moiety, an alkaryl moiety, or an aryl moiety of 1 to about 20 carbon atoms, or an aromatic heterocyclic moiety of 5 to 10 carbon atoms; and $R_2$ is H, a halogen, an alkyl moiety of 1 to about 20 carbon atoms, an alkaryl moiety or an aralkyl moiety of about 5 to about 20 carbon atoms, CN, $N_3$, a protected $NH_2$, $CF_3$, $OCF_3$, an O-alkyl moiety, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, an O-aryl moiety, an S-aryl moiety, an N-aryl moiety, or $O(R_4)$, wherein $R_4$ is a protecting group.

Yet another mononucleoside of the present invention is characterized by formula (1) wherein Z, $R_1$, and B are identical to that described above and Y is a primary amine, a halogen, or $X_1R_3$, wherein $X_1$ is O, S, or Se, and $R_3$ is an alkyl moiety, an aralkyl moiety, a haloalkyl moiety, a haloaryl moiety, an alkaryl moiety, or an aryl moiety of 1 to about 20 carbon atoms, or a aromatic heterocyclic moiety of 5 to 10 carbon atoms; and $R_2$ is a halogen, an alkyl moiety of 1 to about 20 carbon atoms, an alkaryl moiety or an aralkyl moiety of about 5 to about 20 carbon atoms, CN, $N_3$, a protected $NH_2$, $CF_3$, $OCF_3$, an O-alkyl moiety, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, an O-aryl moiety, an S-aryl moiety, an N-aryl moiety, or $O(R_4)$, wherein $R_4$ is a protecting group.

Still another mononucleoside of the present invention is characterized by formula (1) wherein Z, $R_1$, and B are identical to that described above and Y is a primary amine moiety, an O-aralkyl, an S-aryl moiety, a Se-aryl moiety, an S-haloalkyl moiety, a Se-haloalkyl moiety, a branched O-alkyl moiety of 3 to about 10 carbon atoms, or $X_1R_3$, wherein $X_1$ is O, S, or Se, and $R_3$ is an aralkyl moiety, a haloaryl moiety, or an alkaryl moiety of 1 to about 20 carbon atoms, or a aromatic heterocyclic moiety of 5 to 10 carbon atoms; and $R_2$ is a halogen, an alkyl moiety of 1 to about 20 carbon atoms, an alkaryl moiety or an aralkyl moiety of about 5 to about 20 carbon atoms, CN, $N_3$, protected $NH_2$, $CF_3$, $OCF_3$, an O-alkyl moiety, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, O-aryl moiety, S-aryl moiety, an N-aryl moiety, or $O(R_4)$, wherein $R_4$ is a protecting group.

Preferably when Y is an amine moiety, the amine moiety is selected from the groups consisting of $NHR_5$ wherein $R_5$ is a straight chain or branched alkyl moiety, aralkyl moiety, aryl moiety, or alkaryl moiety of 1 to about 20 carbon atoms, a cycloalkyl moiety of 3 to about 8 carbon atoms, or a polycycloalkyl moiety of about 10 to about 30 carbon atoms.

It is further preferred that when Y is an amine moiety, a halogen, or $X_1R_3$, wherein $X_1$ is O, S, or Se, then $R_3$ is $CH_3$ or $CH_2C_6H_4R_6$ wherein $R_6$ is H, a straight chain or a branched alkyl moiety of 1 to about 6 carbon atoms, a straight chain or a branched haloalkyl moiety of 1 to about 6 carbon atoms, a halogen, or $NO_2$.

It is also preferred that when Y is a primary amine moiety, an S-aryl moiety, an Se-aryl moiety, an S-haloalkyl moiety, or an Se-haloalkyl moiety of 1 to about 10 carbon atoms, or Y is a primary amine moiety, an O-aralkyl, an S-aryl moiety, a Se-aryl moiety, an S-haloalkyl moiety, a Se-haloalkyl moiety, a branched O-alkyl moiety of 3 to about 10 carbon atoms, or $X_1R_3$. wherein $X_1$ is O, S, or Se, then $R_3$ is $CH_2C_6H_4R_6$ wherein $R_6$ is H, a straight chain or a branched alkyl moiety of 1 to about 6 carbon atoms, a straight chain or a branched haloalkyl moiety of 1 to about 6 carbon atoms, a halogen, or $NO_2$.

The dinucleosides of the present invention are characterized by formula (3)

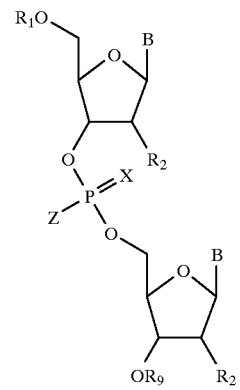

Formula 3 wherein
X is O or S;
Z is an alkyl moiety of about 4 to about 20 carbon atoms, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl;
$R_1$ is a protecting group;
$R_2$ is an alkyl moiety of 1 to about 20 carbon atoms, an alkaryl moiety or an aralkyl moiety of about 5 to about 20 carbon atoms, CN, $N_3$, $NH_2$, $CF_3$, $OCF_3$, an S-alkyl moiety, an N-alkyl moiety, an S-alkenyl moiety, an N-alkenyl moiety, an O-alkynyl moiety, an S-alkynyl moiety, an N-alkynyl moiety, an O-aryl moiety, an S-aryl moiety, or an N-aryl moiety;
$R_9$ is an acyl protecting group, a coupling group, or a silyl protecting group; and
B is a nucleoside base.

The mononucleotide compounds provided above may be synthesized by a variety of methods provided in the present invention. According to one synthesis method, mononucleotide compounds of the present invention are prepared by
 (a) reacting a Z-substituted dichlorophosphine in the presence of a hydrogen chloride scavenger and a nucleoside of formula (2) wherein $R_1$ is a protecting group, $R_2$ is H or an alkoxide moiety of 1 to about 10 carbon atoms, and B is an N-protected nucleoside base, and
 (b) adding aniline and sulfur or selenium or an oxidizing agent to the reaction mixture to produce a mixture of diastereomers of 3'-O-(Z-substituted) phosphonoanilido-thioates, 3'-O-(Z-substituted) phosphonoanilidoselenoates, or 3'-O-(Z-substituted) phosphonoanilidates.

Preferably the oxidizing agent is iodine/2,6-lutidine/$H_2O$, t-butylhydroperoxide, or (±)-(10-camphorsulfonyl) oxaziridine.

Another preferred method of synthesis for mononucleoside compounds of formula (1) wherein Z, $R_1$, and B are as described above,
(2) Y is a primary amine moiety, an S-aryl moiety, an Se-aryl moiety, an S-haloalkyl moiety, or an Se-haloalkyl moiety of 1 to about 10 carbon atoms;
Y is a primary amine moiety, an O-aralkyl, an S-aryl moiety, a Se-aryl moiety, an S-haloalkyl moiety, a Se-haloalkyl moiety, a branched O-alkyl moiety of 3 to about 10 carbon atoms; or
Y is $X_1R_3$, wherein $X_1$ is S or Se, and $R_3$ is $CH_2C_6H_4R_7$ wherein $R_7$ is H, Cl, or $NO_2$ which comprises;
 (a) reacting a Z-substituted dichlorophosphine in the presence of a hydrogen chloride scavenger and a nucleoside of formula (2), wherein $R_1$ is a protecting group, $R_2$ is H or an alkoxide moiety of 1 to about 10 carbon atoms, and B is an N-protected nucleoside base, (b) adding aniline and sulfur or selenium to the reaction mixture to produce a mixture of diastereomers of 3'-O-(Z-substituted) phosphonoanilidothioates, or 3'-O-(Z-substituted) phosphonoanilidoselenoates, (c) reacting the mixture of diastereomers with sodium hydride or with 1,8-diazabicyclo[5.4.0]undec-7-ene and carbon dioxide to produce transient nucleoside (Z-substituted)phosphonothioic acid, or (Z-substituted) phosphonoselenoic acid, and (d) alkylating the transient nucleosides by treatment with an alkylating agent of the formula $R_8W$, wherein $R_8$ is $CH_2C_6H_4R_7$, wherein $R_7$ is H, Cl, or $NO_2$ and W is Cl, Br, or I.

Still another preferred synthesis method for mononucleoside compounds formula (1) wherein Z, $R_1$, and B are identical to that described above and (2) Y is a primary amine moiety, an S-aryl moiety, an Se-aryl moiety, an S-haloalkyl moiety, or an Se-haloalkyl moiety of 1 to about 10 carbon atoms;

Y is a primary amine moiety, an O-aralkyl, an S-aryl moiety, a Se-aryl moiety, an S-haloalkyl moiety, a Se-haloalkyl moiety, a branched O-alkyl moiety of 3 to about 10 carbon atoms; or Y is $X_1R_3$, wherein $X_1$ is O, S, or Se, and $R_3$ is $CH_2C_6H_4R_6$ wherein $R_6$ is H, a straight chain or a branched alkyl moiety of 1 to about 6 carbon atoms, a straight chain or a branched haloalkyl moiety of 1 to about 6 carbon atoms, a halogen, or $NO_2$ which comprises;

(a) reacting Z-substituted dichlorophosphine in the presence of a hydrogen chloride scavenger and a nucleoside of formula (2), wherein $R_1$ is a protecting group, $R_2$ is H or an alkoxide moiety of 1 to about 10 carbon atoms and B is an N-protected nucleoside base, (b) adding aniline and sulfur or selenium to the reaction to produce a mixture of diastereomers of 3'-O-(Z-substituted)phosphonoanilidothioate, or 3'-O-(Z-substituted)phosphonoanilidoselenoate, and (c) oxidizing the mixture of diastereomers by treatment with an oxidizing agent.

Yet another preferred synthesis method for mononucleoside compounds wherein the mononucleoside is characterized by formula (1) wherein Z, $R_1$, and B are identical to that described above and (2) Y is a primary amine moiety, an S-aryl moiety, an Se-aryl moiety, an S-haloalkyl moiety, or an Se-haloalkyl moiety of 1 to about 10 carbon atoms;

Y is a primary amine moiety, an O-aralkyl, an S-aryl moiety, a Se-aryl moiety, an S-haloalkyl moiety, a Se-haloalkyl moiety, a branched O-alkyl moiety of 3 to about 10 carbon atoms; or Y is $X_1R_3$, wherein $X_1$ is S and $R_3$ is $CH_2C_6H_4R_7$ wherein $R_7$ is H, Cl, or $NO_2$ comprises the steps;

(a) reacting Z-substituted dichlorophosphine in the presence of a hydrogen chloride scavenger and a nucleoside of formula (2), wherein $R_1$ is a protecting group, $R_2$ is H or an alkoxide moiety of 1 to about 10 carbon atoms and B is an N-protected nucleoside base, (b) adding aniline and sulfur or selenium to the reaction to produce a mixture of diastereomers of 3'-O-(Z-substitued) phosphonailidothioates, or 3'-O-(Z-subsituted) phosphonanilidoselenoates, (c) oxidizing the mixture of diastereomers by treatment with an oxidizing agent to give oxidized diastereomers, (d) reacting the oxidized diastereomers with sodium hydride or with 1,8-diazabicyclo[5.4.0]undec-7-ene and carbon disulfide to produce transient nucleoside 3'-O-(Z-substituted)phosphonothioic acids, (e) alkylating transient nucleoside 3'-O-(Z-substituted) phosphonothioic acids by treatment with an alkylating agent of the general formula $R_8Z$, wherein $R_8$ is $CH_2C_6H_4R_7$, wherein $R_7$ is H, Cl, or $NO_2$, and Z is Cl, Br, or I.

It is preferred the $R_1$ protecting group of the nucleoside of formula (2) used in the synthesis methods above be methoxymethyl ether, methoxyethoxymethyl ether, 2(-trimethylsilyl)ethoxy ether, acyl, carbamoyl, substituted silyl, 4,4'-dimethoxytrityl, or 9-phenylxanthene-9-oxyl.

It is also preferred that the hydrogen chloride scavengers used in the synthesis methods above be triethylamine, diisopropylethylamine, pyridine, or any tertiary alkyl or aryl amine. Other hydrogen chloride scavenger known to those having skill in the art may also be employed.

In addition it is preferred that where an oxidizing agent is used in a synthesis methods provided above that the oxidizing agent is potassium peroxymonosulfate or hydrogen peroxide.

A variety of methods are provided for the synthesis of diastereomeric mixtures of P-chiral dinucleotides. One synthesis method for the preparation of dinucleotides of formulas (6a) and (6b) comprises the steps;

(a) reacting nucleosides of formulas (8a) and (8b) with sodium hydride or 1,8-diazabicyclo[5.4.0]undec-7-ene and carbon dioxide to form transient nucleoside 3'-O-(Z-substituted)phosphonothioic acids, (b) reacting the transient nucleosides from step (a) with an alkylating agent of the formula $R_8W$, wherein $R_8$ is $CH_2C_6H_4R_7$, wherein $R_7$ is H, Cl, or $NO_2$, and W is Cl, Br, or I, to form nucleoside intermediates of formulas (7a) and (7b)

(c) reacting the nucleoside intermediates with a nucleoside of formula (5) in presence of an activator and a lithium salt in an aprotic organic solvent to form the diastereomeric mixture of P-chiral dinucleosides.

Another method for the synthesis of diastereomeric mixtures of P-chiral dinucleotides for preparing dinucleotides of formulas (6a) and (6b) comprises the steps;

(a) reacting nucleosides of formulas (10a) and (10b) with sodium hydride or 1,8-diazabicyclo[5.4.0]undec-7-ene and carbon dioxide to form transient nucleoside 3'-O-(Z-substituted)phosphonoselenoic acids, (b) reacting the transient nucleosides with an alkylating agent of the formula $R_8W$, wherein $R_8$ is $CH_2C_6H_4R_7$, wherein $R_7$is H, Cl, or $NO_2$, and W is Cl, Br, or I, to form nucleoside intermediates of formulas (11a) and (11b), (c) reacting the nucleoside intermediates with a nucleoside of formula (5) in presence of an activator and a lithium salt in an aprotic organic solvent to form the diastereomeric mixture of P-chiral dinucleosides.

Another method for the synthesis of diastereomeric mixtures of P-chiral dinucleotides for preparing dinucleotides of formulas (6a) and (6b) comprises the steps;

(a) reacting nucleosides of formulas (10a) and (10b) with sodium hydride or 1,8-diazabicyclo[5.4.0]undec-7-ene and carbon dioxide to form transient nucleoside 3'-O-(Z-substituted)phosphonoselenoic acids, (b) reacting the transient nucleosides with an alkylating agent of the formula $R_8W$, wherein $R_8$ is $CH_2C_6H_4R_7$, wherein $R_7$ is H, Cl, or $NO_2$, and W is Cl, Br, or I, to form nucleoside intermediates of formulas (11a) and (11b), (c) reacting the nucleoside intermediates with a nucleoside of formula (5) in presence of an activator and a lithium salt in an aprotic organic solvent to form the diastereomeric mixture of P-chiral dinucleosides.

Still another method for the synthesis of dinucleotides of formulas (6a) and (6b) comprises the steps;

(a) reacting a nucleoside of formula (10a) and (10b) with sodium hydride or 1,8-diazabicyclo[5.4.0]undec-7-ene and carbon dioxide to form transient nucleoside 3'-O-(Z-substituted)phosphonoselenoic acids, (b) reacting the transient nucleosides with an alkylating agent of the formula $R_8W$, wherein $R_8$ is $CH_2C_6H_4R_7$, wherein $R_7$ is H, Cl, or $NO_2$, and W is Cl, Br, or I, to form nucleoside intermediates of formulas (11a) and (11b), (c) reacting the nucleoside intermediates with a nucleoside of formula (5) in presence of an activator and a lithium salt in an aprotic organic solvent to form the diastereomeric mixture of P-chiral dinucleosides.

Yet another method for the synthesis of dinucleotides of formulas (6a) and (6b) wherein $R_1$ is a protecting group; $R_2$ is H, OH, or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety or an atoms, an aminomethyl, or an aminoethyl; and B is an N-protected nucleoside base comprises the steps;

(a) reacting nucleosides of formulas (8a) and (8b) with potassium peroxymonosulfate or hydrogen peroxide to form intermediate nucleosides of formulas (9a) and (9b), (b) reacting the intermediate nucleosides with sodium hydride or DBU and carbon disulfide to form transient nucleoside 3'-O-(Z-substituted)phosphonothioic acids, (c) reacting the transient nucleosides with an alkylating agent of the formula $R_8W$, wherein $R_8$ is $CH_2C_6H_4R_7$, wherein $R_7$ is H, Cl, or $NO_2$, and W is Cl, Br, or I, to form nucleoside intermediates of formulas (7a) and (7b), (d) reacting the nucleoside intermediates from step (a) with a nucleoside of formula (5) in presence of an activator and a lithium salt in an aprotic organic solvent to form the diastereomeric mixture of P-chiral dinucleosides.

Still another method for the synthesis of P-chiral dinucleosides of formulas (6a) and (6b) wherein $R_1$ is a protecting group; $R_2$ is H, OH, or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety or an alkaryl moiety, or an aryl moiety of 1 to about 20 carbon atoms, an aminomethyl, or an aminoethyl; and B is an N-protected nucleoside base comprises the steps;

(a) reacting nucleosides of formulas (10a) and (10b) with potassium peroxymonosulfate or hydrogen peroxide to form the intermediate nucleosides of formulas (9a) and (9b), (b) reacting the intermediate nucleosides with sodium hydride or DBU and carbon diselenide to form transient nucleoside 3'-O-(Z-substituted)phosphonoselenoic acids, (c) reacting the transient nucleosides with an alkylating agent of the formula $R_8W$, wherein $R_8$ is $CH_2C_6H_4R_7$, wherein $R_7$ is H, Cl, or $NO_2$, and W is Cl, Br, or I, to form nucleoside intermediates of formulas (9a) and (9b), (d) reacting the nucleoside intermediates with a nucleoside of formula (5) in presence of an activator and a lithium salt in an aprotic organic solvent to form the diastereomeric mixture of P-chiral dinucleosides.

A variety of synthesis methods are provided for the synthesis of chirally pure dinucleosides. One method for the synthesis of a chirally pure dinucleotide (6a) wherein $R_1$ is a protecting group; $R_2$ is H, OH, or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and B is an N-protected nucleoside base comprises the steps;

(a) reacting a nucleoside of formula (8a) with sodium hydride or 1,8-diazabicyclo[5.4.0]undec-7-ene and carbon dioxide to form a transient nucleoside 3'-O-(Z-substituted) phosphonothioic acid, (b) reacting the transient nucleoside from step (a) with an alkylating agent of the formula $R_8W$, wherein $R_8$ is $CH_2C_6H_4R_7$, wherein $R_7$ is H, Cl, or $NO_2$, and W is Cl, Br, or I, to form a nucleoside intermediate of formula (7a), (c) reacting the nucleoside intermediate from step (b) with a nucleoside of formula (5) in presence of an activator and a lithium salt in an aprotic organic solvent to form the chirally pure dinucleoside.

Another method for the synthesis of a chirally pure dinucleotide (6a) wherein $R_1$ is a protecting group; $R_2$ is H, OH, or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and B is an N-protected nucleoside base comprises the steps;

(a) reacting a nucleoside of formula (10a) with sodium hydride or 1,8-diazabicyclo[5.4.0]undec-7-ene and carbon dioxide to form a transient nucleoside 3'-O-(Z-substituted)phosphonoselenoic acid, (b) reacting the transient nucleoside from step (a) with an alkylating agent of the formula $R_8W$, wherein $R_8$ is $CH_2C_6H_4R_7$, wherein $R_7$ is H, Cl, or $NO_2$, and W is Cl, Br, or I, to form a nucleoside intermediate of formula (11a), (c) reacting the nucleoside intermediate from step (b) with a nucleoside of formula (5) in presence of an activator and a lithium salt in an aprotic organic solvent to form the chirally pure dinucleoside.

Still another method for the synthesis of a chirally pure dinucleotide (6a) wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and (e) B is an N-protected nucleoside base comprises the steps;

(a) reacting a nucleoside of formula (8b) with potassium peroxymonosulfate or hydrogen peroxide to form an intermediate nucleoside of formula (9b), (b) reacting the intermediate nucleoside from step (a) with sodium hydride or DBU and carbon disulfide to form a transient nucleoside 3'-O-(Z-substituted) phosphonothioic acid, (c) reacting the transient nucleoside from step (b) with an alkylating agent of the formula $R_8W$, wherein $R_8$ is $CH_2C_6H_4R_7$, wherein $R_7$ is H, Cl, or $NO_2$, and W is Cl, Br, or I, to form a alkylated nucleoside of formula (7a), (d) reacting the alkylated nucleoside from step (c) with a nucleoside of formula (5) in presence of an activator and a lithium salt in an aprotic organic solvent to form the chirally pure dinucleoside.

Yet another method for the synthesis of chirally pure dinucleotide (6a) wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and (e) B is an N-protected nucleoside base comprises the steps;

(a) reacting a nucleoside of the formula (10b) with potassium peroxymonosulfate or hydrogen peroxide to form a intermediate nucleoside of formula (9b), (b) reacting the intermediate nucleoside from step (a) with sodium hydride or DBU and carbon diselenide to form a transient nucleoside 3'-O-(Z-substituted) phosphonoselenoic acid, (c) reacting the transient nucleoside from step (b) with an alkylating agent of the formula $R_8W$, wherein $R_8$ is $CH_2C_6H_4R_7$, wherein $R_7$ is H, Cl, or $NO_2$, and W is Cl, Br, or I, to form a alkylated nucleoside of formula (11a), (d) reacting the alkylated nucleoside from step (c) with a nucleoside of formula (5) in presence of an activator and a lithium salt in an aprotic organic solvent to form the chirally pure dinucleoside.

A method for the synthesis of chirally pure dinucleotide (6b) wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl or an aminoethyl; and (e) B is an N-protected nucleoside base comprises the steps:

(a) reacting a nucleoside of formula (8b) with sodium hydride or DBU and carbon dioxide to form a transient nucleoside 3'-O-(Z-substituted)phosphonothioic acid, (b) reacting the transient nucleoside from step (a) with an alkylating agent of the formula $R_8W$, wherein $R_8$ is $CH_2C_6H_4R_7$, wherein $R_7$ is H, Cl, or $NO_2$, and W is Cl, Br, or I, to form a nucleoside of formula (7b), (c) reacting the alkylated nucleoside from step (b) with a nucleoside of formula (5) in presence of an activator and a lithium salt in an aprotic organic solvent to form the chirally pure dinucleoside.

Another method for the synthesis of chirally pure dinucleotide (6b) wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and (e) B is an N-protected nucleoside base comprises the steps;

(a) reacting a nucleoside of the formula (10b) with sodium hydride or DBU and carbon dioxide to form a transient nucleoside 3'-O-(Z-substituted)phosphonoselenoic acid, (b) reacting the transient nucleoside from step (a) with an alkylating agent of the formula $R_8W$, wherein $R_8$ is $CH_2C_6H_4R_7$, wherein $R_7$ is H, Cl, or $NO_2$, and W is Cl, Br, or I, to form a nucleoside of formula (11b), (c) reacting the alkylated nucleoside from step (c) with a nucleoside of formula (5) in presence of an activator and a lithium salt in an aprotic organic solvent to form the chirally pure dinucleoside.

Another method for the synthesis of chirally pure dinucleotide (6b) wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and B is an N-protected nucleoside base comprises the steps;

(a) reacting a nucleoside of formula (8a) with potassium peroxymonosulfate or hydrogen peroxide to form an intermediate nucleoside of formula (9a), (b) reacting the intermediate nucleoside from step (a) with sodium hydride or DBU and carbon disulfide to form a transient nucleoside 3'-O-(Z-substituted) phosphonothioic acid, (c) reacting the transient nucleoside from step (b) with an alkylating agent of the formula $R_8W$, wherein $R_8$ is $CH_2C_6H_4R_7$, wherein $R_7$ is H, Cl, or $NO_2$, and W is Cl, Br, or I, to form a nucleoside intermediate of formula (7b), (d) reacting the alkylated nucleoside intermediate from step (c) with a nucleoside of formula (5) in presence of an activator and a lithium salt in an aprotic organic solvent to form the chirally pure dinucleosides.

Yet another method for the synthesis of chirally pure dinucleotide (6b) wherein $R_1$ is a protecting group; $R_2$ is H or alkoxy moiety of 1 to about 10 carbon atoms; $R_9$ is an acyl protecting group, a coupling group, or a silyl protecting group; Z is an alkyl moiety, an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl; and B is an N-protected nucleoside base comprises the steps;

(a) reacting a nucleoside of formula (10a) with potassium peroxymonosulfate or hydrogen peroxide to form an intermediate nucleoside of the formula (9a), (b) reacting the intermediate nucleoside with sodium hydride or DBU and carbon diselenide to form a transient nucleoside 3'-O-(Z-substituted) phosphonoselenoic acid, (c) reacting the transient nucleoside with an alkylating agent of the formula $R_8W$, wherein $R_8$ is $CH_2C_6H_4R_7$, wherein $R_7$ is H, Cl, or $NO_2$, and W is Cl, Br, or I, to form a nucleoside intermediate of formula (11b), (d) reacting the alkylated nucleoside intermediate from step (c) with a nucleoside of formula (5) in presence of an activator and a lithium salt in an aprotic organic solvent to form the chirally pure dinucleosides.

Preferably when the aprotic solvent used in the synthesis methods is acetonuitrile and the activator is 1,8-diazabicyclo [5.4.0]undec-7-ene.

To assist in understanding the present invention, the following examples are included which describe the results of a series of experiments. The following examples relating to this invention should not, of course, be construed as specifically limiting the invention and such variation of the invention, now known or later developed, which would be within the purview of one skilled in the art are considered to fall within the scope of the invention as described herein and hereinafter claimed. According to the following examples are offered by way of illustration and not by way of limitation.

EXAMPLES

Example 1

General Procedure for the Synthesis of Formula 8 (Z=CH$_3$)

To a solution of methyldichlorophosphine (0.29 g, 2.5 mmol) and triethylamine (0.55 g, 5.5 mmol), in THF, cooled to −40° C., was added slowly a solution of the appropriately protected nucleoside (1.0 mmol) in THF (10 mL). After 30 minutes the reaction mixture was allowed to warm to room temperature and aniline (0.28 g, 3.0 mmol) was added dropwise, followed by elemental sulfur. The reaction was followed by tlc and when complete the reaction mixture was diluted with chloroform and extracted with aqueous NaHCO$_3$ solution. The extracts were dried over anhydrous Na$_2$SO$_4$ and concentrated under reduced pressure to provide a crude product that was purified by flash chromatography on silica gel (230–400 mesh) using a mixture of heptane (10–20%) in chloroform. Appropriate fractions were combined and concentrated under reduced pressure to yield the desired product as a mixture of diastereomers.

Example 2

[Rp,Sp]-5'-O-DMT-Thymidine 3'-O-(Methylphosphonoanilidothioate)

The title compound mixture was prepared from 5'-O-DMT-thymidine (0.540 g, 1 mmol) following the general procedure described in Example 1 and was obtained as a solid white foam. Yield: 0.66 g (93%). $^{31}$P NMR (CDCl$_3$) δ 79.44, 79.58; MS (FAB$^-$) m/e 712.4 [(M-H)$^-$].

Example 3

[Rp,Sp]-5'-O-DMT-N$^4$-Benzoyl-2'-Deoxycytidine 3'-O-(Mothylphosphonoanilidothioate)

The title compound mixture was prepared from 5'-O-DMT-N$^4$-benzoyl-2'-deoxycytidine(1 mmol) following the general procedure described in Example 1 and was obtained as a colorless foam. Yield: 70%. $^{31}$P NMR (CDCl$_3$/C$_6$D$_6$) δ 79.38,79.74.

Example 4

[Rp,Sp]-5'-O-DMT-N$^6$-Benzoyl-2'-Deoxyadenosine 3'-O-(Methylphosphonoanilidothiate)

The title compound mixture was prepared from 5'-O-DMT-N$^6$-2'-deoxyadenosine (0.657 g, 1 mmol) ) following the general procedure described in Example 1 and was obtained as a colorless foam. Yield: 75% $^{31}$P NMR (CDCl$_3$) δ 79.21, 79.60.

Example 5

[Rp,Sp]-5'-O-DMT-N$^2$-Isobutyryl-2'-Deoxyguanosine 3'-O-(Methylphonoanilidothioate)

The title compound mixture was prepared from 5'-O-DMT-N$^2$-Isobutyryl-2'-deoxyguanosine (0.640 g, 1 mmol) following the general procedure described in Example 1 and was obtained as a white foam. Yield: 0.71 g (98%) $^{31}$P NMR (CDCL$_3$) δ 79.65, 79.72.

Example 6

[Rp,Sp]-5'-O-DMT-2'-O-Methyl Uridine 3'-O-(Methylphosphonoanilidothioate)

The title compound mixture was prepared from 5'-O-DMT-2'-O-Methyl uridine (0.560 g, 1 mmol) following the general procedure described in Example 1 and was obtained as a colorless foam. Yield: 0.68 g (85%). $^{31}$P NMR (CDCl$_3$) δ 81.96, 81.38.

Example 7

Separation of Diastereomers of Formula 8

Separation of the Rp and Sp diastereomers of Formula 8 described in Examples 2 through 6 was carried out by flash chromatography on silica gel using a mixture of 10–20% heptane in chloroform as eluent.

TABLE 1

| Example/8 | Diastereomer* | $^{31}$P NMR (δ) |
|---|---|---|
| II; B = Thymine | FAST | 79.44 |
|  | SLOW | 79.58 |
| III; B = Cytosine | FAST | 79.38 |
|  | SLOW | 79.74 |
| IV; B = Adenine | FAST | 79.21 |
|  | SLOW | 79.60 |
| V; B = Guanine | FAST | 79.65 |
|  | SLOW | 79.72 |
| VI; B = Uracil | FAST | 81.38 |
|  | SLOW | 81.96 |

*Mobility on Silica gel (Kieselgel 60, 240–400 mesh); eluent CHCl$_3$/MeOH (95:5 v/v)

Example 8

General Procedure for the Synthesis of 5'-O-DMT-(N-Protected) Nucleoside 3'-O-(S-Benzyl Methylphosphonothioates)(Formula 7a and 7b, Z=CH$_3$)

To a stirred solution of the corresponding nucleoside 3'-O-(methylphosphonoanilidothioate) 8 (1 mmol), in dry DMF (10 mL) was added NaH (1.2 molar equivalents) in several portions. Stirring was continued until evolution of hydrogen had ceased. To the resulting slurry was introduced a stream of dry gaseous CO$_2$. The reaction progress was monitored by TLC. Benzyl bromide (5 mmol) was added to the reaction mixture. When the reaction was complete, solvents and excess benzyl bromide were removed by rotary evaporation. The solid residue was dissolved in CHCl$_3$ and washed with saturated aqueous NaHCO$_3$ solution, dried and concentrated. The crude product was purification by flash chromatography on silica gel using 0–5% ethanol in chloroform as eluent. When substrate 8 was reacted as a mixture of diastereomers, the purification process was combined with the separation process to provide pure diastereomers of 7a(SLOW), and 7b(FAST).

Example 9

5'-O-DMT-Thymidine 3'-O-(S-Benzyl Methylphosphonothioate)

The title compound was prepared from 8 (B =Thymine, Z=CH$_3$) (0.712 g, 1 mmol) following the general procedures

Example 10

5'-O-DMT-N⁴-Benzoyl-2'-Deoxycytidine 3'-O- (S-Benzyl Methylphosphonothioate)

The title compound was prepared from 8 (B=Cytosine, Z=CH$_3$) (1 mmol), following the general procedures described in Example 8. Yield: 82%. $^{31}$P NMR (CDCl$_3$) δ 55.41, 55.21.

Example 11

5'-O-DMT-N⁶-Benzoyl-2'-Deoxyadenosine 3'-O-(S-Benzyl Methylphosphonothioate)

The title compound was prepared from 8 (B=Adenine, Z=CH$_3$) (1 mmol), following the general procedure described in Example 8. Yield: 75%. $^{31}$P NMR (CH$_2$Cl$_2$/C$_6$D$_6$) δ 55.80, 55.21 ppm.

Example 12

5'-O-DMT-N⁴-Isobutyryl-2'-Deoxyguanosine 3'-O-(S-Benzyl Methylphosphonothioate)

The title compound was prepared from 8 (B=guanine, Z=CH$_3$) (1 mmol) following the general procedure described in Example 8. Yield: 75% $^{31}$P NMR (CDCl$_3$) δ 56.01, 55.85.

Example 13

Oxidation of (FAST) 5'-O-DMT-Thymidine 3'-O-(Methylphosphonothioanilidate) 8a to (FAST) 5'-O-DMT-Thymidine 3'-O-(Methanephosphonoanilidate) 9a Using Potasium Peroxymonosulfate.

To a solution of compound 8a (FAST) (0.072 g, 1 mmol) in a mixture of MeOH and THF was added an aqueous solution of Potasium Peroxymonosulfate (pH 6.7–7, 2 mmols). After 10 minutes a solution of 10% aqueous Na$_2$S$_2$O$_3$ was added and the mixture was extracted with chloroform. The extracts were dried over anhydrous Na$_2$SO$_4$ and concentrated. The crude product was purified by flash chromatography on silica gel using a mixture of 10–20% heptane in chloroform as eluent to afford 0.047 g (73%) of diastereomerically pure (Fast)-9a. $^{31}$P NMR (CDCl$_3$) δ 30.1. MS (FAB−) m/e 696.4 [(M-H)⁻].

Example 14

Oxidation of (SLOW) 5'-O-DMT-Thymidine 3'-O-(Methylphosphonothioanilidate) 8b to (SLOW) 5'-O-DMT-Thymidine 3'-O-(Methanephosphonoanilidate) Using Potasium Peroxymonosulfate Conversion of 8b (SLOW) to 9b (SLOW) was carried out using procedures analogous to those described in Example 13. Yield: 70%; $^{31}$P NMR (CDCl$_3$) δ 29.89.

Example 15

Conversion of 5'-O-DMT-Thymidine 3'-O-Methanephosphonoanilidate 9 to 5'-O-DMT-Thymidine 3'-O-(S-Benzyl Methanephosphonothioate) 7

Compounds 9 (FAST or SLOW) were dried prior to reaction and then dissolved in THF (2 mL). To this solution was added 1,8-diazabicyclo[5.4.0]undec-7-ene (DBU) (0.02 mL) and the reaction mixture was stirred at ambient temperature for 45 minutes, followed by addition of CS$_2$ (1 mL). After 20 minutes benzyl bromide was added (5 equivalents) and the reaction progress was monitored by tlc. When the reaction was complete the mixture was diluted with water and extracted with chloroform. The extracts were dried over anhydrous Na$_2$SO$_4$ and concentrated. The crude product was purified by flash chromatography on silica gel using 0–5% ethanol in chloroform as eluent.

From compound 9a (FAST), product 7b (FAST) was obtained in 65% yield. $^{31}$P NMR (CDCl$_3$) δ 56.85. Compound 9b (SLOW) was converted to 7a (SLOW) in 70% yield. $^{31}$P NMR (CDCl$_3$) δ 55.38.

Example 16

General Procedure for the Synthesis of Dinucleoside(3',5')Methylphosphonates (FAST)–6a or (SLOW)–6b (Z=CH$_3$)

The corresponding diastereomerically pure compounds 7 (SLOW or FAST) (0.3 mmol) and 3'-O-acetyl (N-protected)-2'-deoxynucleoside 5 (0.1 mmol) were dried prior to reaction and then dissolved in dry pyridine (5 mL). To this solution was added lithium chloride (0.125 g, 3 mmol), followed by a solution of DBU (0.456 g, 3 mmol) in pyridine (1.5 mL) in one portion. The reaction was stirred at room temperature and its progress was monitored by tlc. After the reaction was complete, solvent was evaporated and the oily residue was dissolved in chloroform and extracted with phosphate buffer. The organic extracts were dried over anhydrous Na$_2$SO$_4$ and concentrated. The crude product was purified by flash chromatography on silica gel using a mixture of 0–3% ethanol in chloroform as eluent.

Example 17

Synthesis of (FAST)-5'-O-DMT-Thymidylyl-(3'D5')-3'-O-Acetylthymidine 3'-Methylphosphonate The title compound was prepared from the corresponding compound (SLOW)–7a following the general procedure described in Example 16. Yield: 85% $^{31}$P NMR (CDCl$_3$) δ 33.00. $^1$H NMR (CDCl$_3$) δ 1.58 (d, J$_{P-H}$=17.64 Hz, 3H, P—CH$_3$), MS (FAD⁻) m/e 887 [(M-H)⁻].

Example 18

(FAST)-N⁴-Benzoyl-5'-O-DMT-2'-Deoxycytidylyl-(3'D, 5') -N⁴ -Benzoyl- 3'-O-Acetyl-2'-Deoxycytidine 3'-Methylphosphonate The title compound was prepared from the corresponding compound (SLOW)–7a following the general procedure described in Example 16. Yield: 73%. $^{31}$P NMR (CDCl$_3$) δ 33.08. $^1$H NMR (CDCl$_3$) δ 1.6 (d, J$_{P-H}$=17.5 Hz, 3H, P—CH$_3$).

Ms (FAB⁻) m/e 1067 [(M-H)⁻].

We claim:
1. A compound having the formula

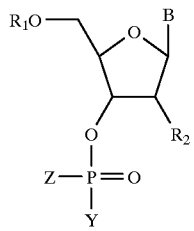

wherein
(a) Y is a primary amine moiety, an S-aryl moiety, an Se-aryl moiety, an S-haloalkyl moiety, or an Se-haloalkyl moiety of 1 to about 10 carbon atoms, or $XIR_3$, wherein $X_1$ is O, S, or Se, and $R_3$ is an aralkyl moiety, a haloaryl moiety, or an alkaryl moiety of 6 to about 20 carbon atoms, or an aromatic heterocyclic moiety of 5 to 10 carbon atoms;
(b) Z is an aralkyl moiety, a haloalkyl moiety, an alkenyl moiety, or an alkaryl moiety of 1 to about 20 carbon atoms, an aminomethyl, or an aminoethyl;;
(c) $R_1$ is a protecting group;
(d) $R_2$ is H, a halogen, an alkyl moiety of 1 to about 20 carbon atoms, an alkaryl moiety or an aralkyl moiety of about 5 to about 20 carbon atoms, CN, $N_3$, a protected $NH_2$, $CF_3$, $OCF_3$, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, an O-aryl moiety, an S-aryl moiety, an N-aryl moiety, or $(O)R_4$, wherein $R_4$ is a protecting group; and
(e) B is an optionally protected nucleoside base.

2. A compound having the formula

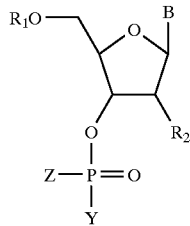

wherein
(a) Y is an amine moiety, a halogen, or $X_1R_3$, wherein $X_1$ is O, S or Se,, and $R_3$ is an alkyl moiety, an aralkyl moiety, a haloalkyl moiety, a haloaryl moiety, an alkaryl moiety, or an aryl moiety of 1 to about 20 carbon atoms, or an aromatic heterocyclic moiety of 5 to 10 carbon atoms;
(b) Z is an alkyl moiety, an aralkyl moiety, a haloalkyl moiety, an alkenyl moiety, an alkynyl moiety, an alkyl moiety, or an aryl moiety of 1 to about 20 carbon atoms, an aminomethyl, or an aminoethyl;
(c) $R_1$ is a protecting group other than —COPh;
(d) $R_2$ is H, a halogen, an alkyl moiety of 1 to about 20 carbon atoms, an alkaryl moiety or an aralkyl moiety of about 5 to about 20 carbon atoms, CN, $N_3$, a protected $NH_2$, $CF_3$, $OCF_3$, an O-alkyl moiety, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, an O-aryl moiety, an S-aryl moiety, an N-aryl moiety, or $(O)R_4$, wherein $R_4$ is a protecting group; and
(e) B is an optionally protected nucleoside base.

3. A compound having the formula

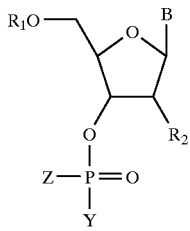

wherein
(a) Y is a primary amine, a halogen, or $X_1R_3$, wherein $X_1$ is O, S or Se, and $R_3$ is an alkyl moiety, an aralkyl moiety, a haloalkyl moiety, a haloaryl moiety, an alkaryl moiety, or an aryl moiety of 1 to about 20 carbon atoms, or an aromatic heterocyclic moiety of 5 to 10 carbon atoms;
(b) Z is an aralkyl moiety, a haloalkyl moiety, an alkenyl moiety, an alkynyl moiety, an alkaryl moiety, or an aryl moiety of 1 to about 20 carbon atoms, an aminomethyl, or an aminoethyl;
(c) $R_1$ is a protecting group;
(d) $R_2$ is a halogen, an alkyl moiety of 1 to about 20 carbon atoms, an alkaryl moiety or an aralkyl moiety of about 5 to about 20 carbon atoms, CN, $N_3$, a protected $NH_2$, $CF_3$, $OCF_3$, an O-alkyl moiety, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, an O-aryl moiety, an S-aryl moiety, an N-aryl moiety, or $(O)R_4$, wherein $R_4$ is a protecting group; and
(e) B is an optionally protected nucleoside base.

4. A compound having the formula

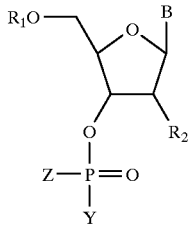

wherein
(a) Y is a primary amine moiety, an O-aralkyl, an S-aryl moiety, an Se-aryl moiety, an S-haloalkyl moiety, an Se-haloalkyl moiety, a branched O-alkyl moiety of 3 to about 10 carbon atoms, or $X_1 R_3$, wherein $X_1$ is O, S, or Se, and $R_3$ is an aralkyl moiety, a haloaryl moiety, or an alkaryl moiety of 1 to about 20 carbon atoms, or an aromatic heterocyclic moiety of 5 to 10 carbon atoms;
(b) Z is an aralkyl moiety, a haloalkyl moiety, an alkenyl moiety, an alkynyl moiety, an alkaryl moiety or an aryl moiety of 1 to about 20 carbon atoms, an aminomethyl, or an aminoethyl;
(c) $R_1$ is a protecting group;
(d) $R_2$ is a halogen, an alkyl moiety of 1 to about 20 carbon atoms, an alkaryl moiety or an aralkyl moiety of about 5 to about 20 carbon atoms, CN, $N_3$, a protected $NH_2$, $CF_3$, $OCF_3$, an O-alkyl moiety, an S-alkyl moiety, an N-alkyl moiety, an O-alkenyl moiety, an S-alkenyl moiety, an N-alkenyl moiety, an O-alkynyl moiety, an S-alkynyl moiety, an N-alkynyl moiety, an O-aryl moiety, an S-aryl moiety, an N-aryl moiety, or $(O)R_4$, wherein $R_4$ is a protecting group; and (e) B is an optionally protected nucleoside base.

5. A compound according to any of claims 1, 2, 3 or 4, wherein Y is primary amine moiety $NHR_5$ wherein $R_5$ is a straight chain or a branched alkyl moiety, an aralkyl moiety, an aryl moiety, or an alkaryl moiety of 1 to about 20 carbon atoms, a cycloalkyl moiety of 3 to about 8 carbon atoms, or a polycycloalkyl moiety of about 10 to about 30 carbon atoms.

6. A compound according to any of claims 2 or 3, wherein $R_3$ is $CH_3$ or $CH_2C_6H_4R_6$ wherein $R_6$ is H, a straight chain or a branched alkyl moiety of 1 to about 6 carbon atoms, a straight chain or a branched haloalkyl moiety of 1 to about 6 carbon atoms, a halogen, or $NO_2$.

7. A compound according to any of claims 1 or 4, wherein $R_3$ is $CH_2C_6H_4R_6$ wherein $R_6$ is H, a straight chain or a branched alkyl moiety of 1 to about 6 carbon atoms, a straight chain or a branched haloalkyl moiety of 1 to about 6 carbon atoms, a halogen, or $NO_2$.

8. A method for the synthesis of a compound according to any of claims 1, 2, 3, or 4 comprising the steps of;

(a) reacting a Z-substituted dichlorophosphine in the presence of a hydrogen chloride scavenger and a nucleoside of formula (2), wherein $R_1$ is a protecting group; $R_2$ is H or an alkoxide moiety of 1 to about 10 carbon atoms; and B is an N-protected nucleoside base, and (b) adding aniline and sulfur or selenium or an oxidizing agent to the reaction mixture to produce a mixture of diastereomers of 3'-O-(Z-substituted) phosphonoanilidothioates, 3'-O-(Z-substituted) phosphonoanilidoselenoates, or 3'-O-(Z-substituted) phosphonoanilidates.

9. A method according to claim 8, wherein the oxidizing agent is selected from the group consisting of iodine/2,6-lutidine/$H_2O$, t-butylhydroperoxide, or (±)-(10-camphorsulfonyl)oxaziridine.

10. A method for the synthesis of a compound according to any of claims 1 or 4, wherein Y is $X_1R_3$, wherein $X_1$, is S or Se and $R_3$ is $CH_2C_6H_4R_7$, wherein $R_7$ is H, Cl, or $NO_2$, comprising the steps of;

(a) reacting a Z-substituted dichlorophosphine in the presence of a hydrogen chloride scavenger and a nucleoside of formula (2), wherein $R_1$ is a protecting group, $R_2$ is H or an alkoxide moiety of 1 to about 10 carbon atoms, and B is an N-protected nucleoside base, (b) adding aniline and sulfur or selenium to the reaction mixture to produce a mixture of diastereomers of 3'-O-(Z-substituted)phosphonoanilidothioates, or 3'-O-(Z-substituted)phosphonoanilidoselenoates, (c) reacting the mixture of diastereomers with sodium hydride or with 1,8-diazabicyclo[5.4.0]undec-7-ene and carbon dioxide to produce transient nucleoside (Z-substituted)phosphonothioic acids or (Z-substituted) phosphonoselenoic acids, and (d) alkylating the transient nucleosides from step (c) by treatment with an alkylating agent of the formula $R_8W$, wherein $R_8$ is $CH_2C_6H_4R_7$, wherein $R_7$ is H, Cl, or $NO_2$ and W is Cl, Br, or I.

11. A method for the synthesis of a compound according to any of claims 1 or 4 comprising the steps of;

(a) reacting Z-substituted dichlorophosphine in the presence of a hydrogen chloride scavenger and a nucleoside of formula (2), wherein $R_1$ is a protecting group; $R_2$ is H or an alkoxide moiety of 1 to about 10 carbon atoms; and B is an N-protected nucleoside base, (b) adding aniline and sulfur or selenium to the reaction to produce a mixture of diastereomers of 3'-O-(Z-substituted)phosphonoanilidothioate, or 3'-O-(Z-substituted)phosphonoanilidoselenoate, and (c) oxidizing the mixture of diastereomers by treatment with an oxidizing agent.

12. A method for the synthesis of a compound according to any of claims 1 or 4, wherein Y is $X_1R_3$ wherein $X_1$ is S and $R_3$ is $CH_2C_6H_4R_7$, wherein $R_7$ is H, Cl, or $NO_2$, comprising the steps of:

(a) reacting Z-substituted dichlorophosphine in the presence of a hydrogen chloride scavenger and a nucleoside of formula (2), wherein $R_1$ is a protecting group; $R_2$ is H or an alkoxide moiety of 1 to about 10 carbon atoms; and B is an N-protected nucleoside base, (b) adding aniline and sulfur or selenium to the reaction to produce a mixture of diastereomers of 3'-O-(Z-substituted) phosphonoanilidothioates, or 3'-O-(Z-substituted) phosphonoanilidoselenoates, (c) oxidizing the mixture of diastereomers by treatment with an oxidizing agent to give oxidized diastereomers, (d) reacting the oxidized diastereomers with sodium hydride or with 1,8-diazabicyclo[5.4.0]undec-7-ene and carbon disulfide to produce a transient nucleoside 3'-O(Z-substituted)phosphonothioic acid, and (e) alkylating the transient nucleoside 3'-a-(Z-substituted) phosphonothioic acid by treatment with an alkylating agent of the general formula $R_8Z$, wherein $R_8$ is $CH_2C_6H_4R_7$ wherein $R_7$ is H, Cl, or $NO_2$, and Z is Cl, Br, or I.

13. A method according to claim 8 wherein $R_1$ is a protecting group selected from the group consisting of methoxymethyl ether, methoxyethoxymethyl ether, 2(-trimethylsilyl) ethoxy ether, acyl, carbamoyl, substituted silyl, 4,4'-dimethoxytrityl, and 9-phenylxanthene-9-oxyl.

14. A method according to claim 9 wherein the hydrogen chloride scavenger is selected from the group consisting of triethylamine, diisopropylethylamine, pyridine, tertiary alkyl amine and tertiary aryl amine.

15. A method according to claim 8 wherein the oxidizing agent is potassium peroxymonosulfate or hydrogen peroxide.

16. A method according to claim 10 wherein $R_1$ is a protecting group selected from the group consisting of methoxymethyl ether, methoxyethoxymethyl ether, 2(-trimethylsilyl) ethoxy ether, acyl, carbamoyl, substituted silyl, 4,4'-dimethoxytrityl, and 9-phenylxanthene-9-oxyl.

17. A method according to claim 11 wherein $R_1$ is a protecting group selected from the group consisting of ether, methoxyethoxymethyl ether, 2(-trimethylsilyl) ethoxy ether, acyl, carbamoyl, substituted silyl, 4,4'-dimethoxytrityl, and 9-phenylxanthene-9-oxyl.

18. A method according to claim 12 wherein $R_1$ is a protecting group selected from the group consisting of methoxymethyl ether, methoxyethoxymethyl ether, 2(-trimethylsilyl) ethoxy ether, acyl, carbamoyl, substituted silyl, 4,4'-dimethoxytrityl, and 9-phenylxanthene-9-oxyl.

19. A method according to claim 10 wherein the hydrogen chloride scavenger is selected from the group consisting of triethylamine, diisopropylethylamine, pyridine, tertiary alkyl amine and tertiary aryl amine.

20. A method according to claim 11 wherein the hydrogen chloride scavenger is selected from the group consisting of triethylamine, diisopropylethylamine, pyridine, tertiary alkyl amine and tertiary aryl amine.

21. A method according to claim 12 wherein the hydrogen chloride scavenger is selected from the group consisting of triethylamine, diisopropylethylamine, pyridine, tertiary alkyl amine and tertiary aryl amine.

22. A method according to claim 11 wherein the oxidizing agent is potassium peroxymonosulfate or hydrogen peroxide.

23. A method according to claim 12 wherein the oxidizing agent is potassium peroxymonosulfate or hydrogen peroxide.

* * * * *